(12) United States Patent
Lynch et al.

(10) Patent No.: US 10,301,575 B2
(45) Date of Patent: *May 28, 2019

(54) CONSUMER PRODUCT COMPOSITION COMPRISING A POLYETHYLENE GLYCOL CARRIER WITH SILICONE PARTICLES DISPERSED THEREIN

(71) Applicant: The Procter & Gamble Company, Cincinnati, OH (US)

(72) Inventors: Matthew Lawrence Lynch, Mariemont, OH (US); Joanne Roberta Willman, Fairfield, OH (US); Brandon Philip Illie, Felicity, OH (US); Kevin Graham Blyth, Whitley Bay (GB); Carola Barrera, West Chester, OH (US); Philip Andrew Sawin, Cincinnati, OH (US); Robert Wayne Glenn, Jr., Liberty Township, OH (US); Yousef Georges Aouad, Cincinnati, OH (US); Janine Anne Flood, Cincinnati, OH (US); Benjamin John Kutay, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/097,310

(22) Filed: Apr. 13, 2016

(65) Prior Publication Data
US 2016/0304812 A1   Oct. 20, 2016

Related U.S. Application Data

(60) Provisional application No. 62/147,150, filed on Apr. 14, 2015.

(51) Int. Cl.
| | | |
|---|---|---|
| *C11D 3/00* | (2006.01) |
| *A61Q 5/02* | (2006.01) |
| *A61Q 5/12* | (2006.01) |
| *A61Q 19/00* | (2006.01) |
| *A61K 8/86* | (2006.01) |
| *A61K 8/891* | (2006.01) |
| *A61K 8/898* | (2006.01) |
| *A61K 8/02* | (2006.01) |
| *C11D 3/37* | (2006.01) |
| *C11D 17/06* | (2006.01) |
| *C11D 3/20* | (2006.01) |
| *C11D 17/00* | (2006.01) |

(52) U.S. Cl.
CPC ........... *C11D 3/001* (2013.01); *A61K 8/0245* (2013.01); *A61K 8/86* (2013.01); *A61K 8/891* (2013.01); *A61K 8/898* (2013.01); *A61Q 5/02* (2013.01); *A61Q 5/12* (2013.01); *A61Q 19/00* (2013.01); *C11D 3/2093* (2013.01); *C11D 3/373* (2013.01); *C11D 3/3707* (2013.01); *C11D 3/3742* (2013.01); *C11D 3/3749* (2013.01); *C11D 17/0034* (2013.01); *C11D 17/06* (2013.01); *A61K 2800/654* (2013.01)

(58) Field of Classification Search
CPC ...................................................... C11D 3/001
See application file for complete search history.

(56) References Cited

U.S. PATENT DOCUMENTS

| | | | |
|---|---|---|---|
| 4,077,890 A | 3/1978 | Barker |
| 4,096,072 A | 6/1978 | Brock et al. |
| 4,152,272 A | 5/1979 | Young |
| 4,176,079 A | 11/1979 | Geurry et al. |
| 4,652,392 A | 3/1987 | Baginski et al. |
| 4,765,916 A | 8/1988 | Ogar, Jr. et al. |
| 5,154,849 A | 10/1992 | Visscher et al. |
| 5,173,200 A | 12/1992 | Kellett |
| 5,362,483 A | 11/1994 | Morgan et al. |
| 5,759,208 A | 6/1998 | Zhen |
| 5,770,556 A | 6/1998 | Farrell et al. |
| 5,783,536 A | 7/1998 | Farrell et al. |

(Continued)

FOREIGN PATENT DOCUMENTS

| | | |
|---|---|---|
| AU | 2012201719 A1 | 4/2012 |
| CA | 2044043 C | 4/1998 |

(Continued)

OTHER PUBLICATIONS

International Search Report and Written Opinion dated Jun. 16, 2016, 11 pgs.
International Search Report and Written Opinion dated May 31, 2016, 15 pgs.
International Search Report and Written Opinion dated Jun. 7, 2016, 15 pgs.
International Search Report and Written Opinion dated Jun. 1, 2016, 13 pgs.
All Office Actions, U.S. Appl. No. 15/097,305, filed Oct. 20, 2016.
All Office Actions, U.S. Appl. No. 15/097,307, filed Oct. 20, 2016.
All Office Actions, U.S. Appl. No. 15/097,302, filed Oct. 20, 2016.
All Office Actions, U.S. Appl. No. 15/097,308, filed Oct. 20, 2016.

(Continued)

*Primary Examiner* — Charles I Boyer
(74) *Attorney, Agent, or Firm* — Gary J. Foose

(57) ABSTRACT

A consumer product composition comprises a non-porous dissolvable solid structure comprising from about 30% to about 95%, by weight of the consumer product composition, of a carrier material, and from about 5% to about 50%, by weight of the consumer product composition, of a hydrophobic conditioning agent disposed within the carrier material of the non-porous dissolvable solid structure. The carrier material comprises a polyethylene glycol material, or mixtures thereof, having a molecular weight of from about 200 to about 50,000. The hydrophobic conditioning agent is selected from the group consisting of silicone materials, organic conditioning oils, hydrocarbon oils, fatty esters, metathesized unsaturated polyol esters, silane-modified oils, and mixtures thereof.

25 Claims, 6 Drawing Sheets
(1 of 6 Drawing Sheet(s) Filed in Color)

(56) References Cited

U.S. PATENT DOCUMENTS

| | | | |
|---|---|---|---|
| 5,935,917 A * | 8/1999 | Farrell | C11D 1/94 510/141 |
| 6,174,845 B1 * | 1/2001 | Rattinger | A61K 8/02 510/141 |
| 6,254,892 B1 | 7/2001 | Duccini et al. | |
| 6,465,407 B2 | 10/2002 | Hayashi et al. | |
| 6,699,826 B1 | 3/2004 | Saijo et al. | |
| 6,703,011 B2 | 3/2004 | Shefer et al. | |
| 6,818,606 B1 | 11/2004 | Hanada et al. | |
| 7,091,171 B2 | 8/2006 | Caswell et al. | |
| 7,208,460 B2 | 4/2007 | Shefer | |
| 7,544,651 B2 | 6/2009 | Caswell et al. | |
| 7,674,758 B2 | 3/2010 | Wahl et al. | |
| 7,700,530 B2 | 4/2010 | Mundschau et al. | |
| 7,786,027 B2 | 8/2010 | Aouad et al. | |
| 7,786,069 B2 | 8/2010 | Tindel-Koukal et al. | |
| 7,867,968 B1 | 1/2011 | Aouad | |
| 7,871,976 B1 | 1/2011 | Aouad | |
| 8,398,961 B2 | 3/2013 | Kaplan et al. | |
| 8,497,234 B2 | 7/2013 | Mayer et al. | |
| 9,150,819 B2 * | 10/2015 | Wetrosky | C11D 1/62 |
| 2004/0253434 A1 | 12/2004 | Patel et al. | |
| 2005/0005591 A1 | 1/2005 | Wieger et al. | |
| 2005/0170996 A1 | 8/2005 | Blyth et al. | |
| 2005/0202999 A1 | 9/2005 | Morgan, III et al. | |
| 2006/0217288 A1 | 9/2006 | Wahl et al. | |
| 2006/0276370 A1 | 12/2006 | Zhang et al. | |
| 2007/0054815 A1 | 3/2007 | Convents et al. | |
| 2007/0259170 A1 | 11/2007 | Brown et al. | |
| 2007/0286904 A1 | 12/2007 | Poppelwell et al. | |
| 2009/0042766 A1 | 2/2009 | Mayer et al. | |
| 2009/0281011 A1 | 11/2009 | Mayer et al. | |
| 2010/0204341 A1 | 8/2010 | Yu et al. | |
| 2010/0278886 A1 | 11/2010 | Yu et al. | |
| 2011/0165110 A1 * | 7/2011 | Kinoshita | A61K 8/042 424/70.27 |
| 2012/0175016 A1 | 7/2012 | Lopez et al. | |
| 2012/0258902 A1 | 10/2012 | Parrish et al. | |
| 2013/0095156 A1 | 4/2013 | Barnhart et al. | |
| 2013/0095717 A1 | 4/2013 | Vanblarcom et al. | |
| 2014/0115794 A1 * | 5/2014 | Christensen | C11D 1/62 8/137 |
| 2014/0179587 A1 | 6/2014 | Brown | |
| 2015/0376548 A1 * | 12/2015 | Wetrosky | C11D 1/62 8/137 |
| 2016/0145537 A1 * | 5/2016 | Blattner | C11D 3/001 510/516 |
| 2016/0145539 A1 * | 5/2016 | Blattner | C11D 3/001 510/516 |
| 2016/0298058 A1 * | 10/2016 | Christensen | C11D 1/62 |
| 2016/0304808 A1 | 10/2016 | Lynch et al. | |
| 2016/0304809 A1 | 10/2016 | Lynch et al. | |
| 2016/0304810 A1 | 10/2016 | Lynch et al. | |
| 2016/0304811 A1 | 10/2016 | Lynch et al. | |
| 2016/0304812 A1 | 10/2016 | Lynch et al. | |
| 2016/0304819 A1 | 10/2016 | Lynch et al. | |

FOREIGN PATENT DOCUMENTS

| | | |
|---|---|---|
| DE | 19904233 | 8/2000 |
| DE | 102007059296 A1 | 6/2009 |
| EP | 0334430 | 9/1989 |
| EP | 211589 B1 | 11/1990 |
| EP | 1201745 A1 | 5/2002 |
| IN | 200301 B | 8/2007 |
| KR | 2012021449 A | 3/2012 |
| WO | 97/49381 * | 12/1997 |
| WO | WO 9749381 A1 | 12/1997 |
| WO | WO 2001016280 A2 | 3/2001 |
| WO | WO 2005/005591 | 1/2005 |
| WO | WO 2006088980 A1 | 8/2006 |
| WO | 2008009521 * | 1/2008 |
| WO | WO 2008009521 A1 | 1/2008 |
| WO | WO 2009006218 A2 | 1/2009 |
| WO | WO 2013036662 | 3/2013 |
| WO | WO 2014099879 A1 | 6/2014 |
| WO | WO 2016/078941 | 5/2016 |
| WO | WO 2016/078942 | 5/2016 |
| WO | WO 2016081006 | 5/2016 |

OTHER PUBLICATIONS

All Office Actions, U.S. Appl. No. 15/097,310, filed Oct. 20, 2016.
All Office Actions for U.S. Appl. No. 15/097,305, filed Apr. 13, 2016.
All Office Actions for U.S. Appl. No. 15/097,306, filed Apr. 13, 2016.
All Office Actions for U.S. Appl. No. 15/097,307, filed Apr. 13, 2016.
All Office Actions for U.S. Appl. No. 15/097,308, filed Apr. 13, 2016.
All Offices Actions for U.S. Appl. No. 15/097,302, filed Apr. 13, 2016.

* cited by examiner

CONSUMER PRODUCT COMPOSITION COMPRISING A POLYETHYLENE GLYCOL CARRIER WITH SILICONE PARTICLES DISPERSED THEREIN

FIELD OF THE INVENTION

The present invention relates to a consumer product composition comprising a non-porous dissolvable solid structure and a hydrophobic conditioning agent disposed therein.

BACKGROUND OF THE INVENTION

Consumer product compositions often contain benefit agents, such as conditioning agents, to provide enhancements to surfaces treated with the consumer product composition such as improved hand feel benefits (e.g. soft, silky feel), softness benefits, and the like. Such benefits are desired by consumers of fabric care products, such as laundry detergents or fabric softeners, skin care products, such as skin moisturizing lotions, and hair care products, like shampoo or hair conditioners.

Such consumer product compositions, such as fabric softeners or hair conditioners, are typically provided in the form of aqueous liquid products. Since many desirable conditioning agents are hydrophobic in nature, it can be a challenge to create a stable aqueous liquid formulation containing hydrophobic conditioning agents. As a result, such conditioning agents are typically incorporated in aqueous liquid compositions in the form of emulsions or other systems comprising emulsion droplets/particles having relatively small particle size benefits agents, typically smaller than 1 μm. One drawback of having small particle size conditioning agents is that it can be difficult to deposit and retain small particle size benefit agents on the treated surface, especially if the surfaces are being treated in the context of an aqueous treatment liquor such as a detergent treatment liquor in a washing machine or a treatment liquor that a consumer uses in the shower when shampooing and/or conditioning her hair. As a result, the small particle size conditioning agents can be easily washed down the drain and therefore wasted, as opposed to being deposited and retained on surfaces to enhance the surface.

In order to address such drawbacks, attempts have been made to provide delivery systems, such as encapsulation systems, for the hydrophobic conditioning agents in order to enhance their deposition and retention on surfaces while remaining stable in an aqueous liquid product. These delivery systems, however, can limit the effectiveness of the conditioning agents or lead to other issues.

It is therefore desired to provide a consumer product composition that contains relatively large particle size conditioning agents without the need for liquid delivery systems that can interfere with the effectiveness of the conditioning agent being deposited on the treated surfaces.

SUMMARY OF THE INVENTION

The present invention relates to a consumer product composition comprising a non-porous dissolvable solid structure comprising from about 30% to about 95%, by weight of the consumer product composition, of a carrier material, and from about 5% to about 50%, by weight of the consumer product composition, of a hydrophobic conditioning agent disposed within the carrier material of the non-porous dissolvable solid structure. The carrier material comprises a polyethylene glycol material, or mixtures thereof, having a molecular weight of from about 200 to about 50,000. The hydrophobic conditioning agent is selected from the group consisting of silicone materials, organic conditioning oils, hydrocarbon oils, fatty esters, metathesized unsaturated polyol esters, silane-modified oils, and mixtures thereof.

The non-porous dissolvable solid structure comprises carrier material within which the hydrophobic conditioning agent is disposed. The carrier material is selected such that the desired mean particle size of the hydrophobic conditioning agent can be "set" in the carrier material of the non-porous dissolvable solid structure. The desired mean particle size of hydrophobic conditioning agent in the consumer product composition will generally be in the range of from about 2 μm to about 2,000 μm. The optimal particle size of the hydrophobic conditioning agent may depend upon the intended use of the consumer product composition. For instance, a fabric softening product composition for conditioning fabrics in a laundry process will preferably contain a hydrophobic conditioning agent having a mean particle size of from about 2 μm to about 500 μm, more preferably from about 2 μm to about 120 μm, more preferably from about 2 um to about 70 um; whereas a hair conditioning product composition for conditioning hair in a hair washing process will preferably contain a hydrophobic conditioning agent having an average particle size of from about 10 μm to about 2,000 μm. Since the consumer product composition is in a solid, non-porous form, the mean particle size of the hydrophobic conditioning agent will generally remain constant during packaging, shipping and storage of the consumer product composition.

When the consumer product composition is ready for use, it can be dissolved in an aqueous solution to form an aqueous treatment liquor. Upon dissolution, the hydrophobic conditioning agent will tend to maintain its mean particle size from the consumer product composition and into the aqueous treatment liquor. The relatively large particles of hydrophobic conditioning agent in the aqueous treatment liquor will tend to be more effectively deposited on the treated surfaces and therefore provide enhanced consumer benefits, as compared to products which provide smaller mean particle size agents.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1A:
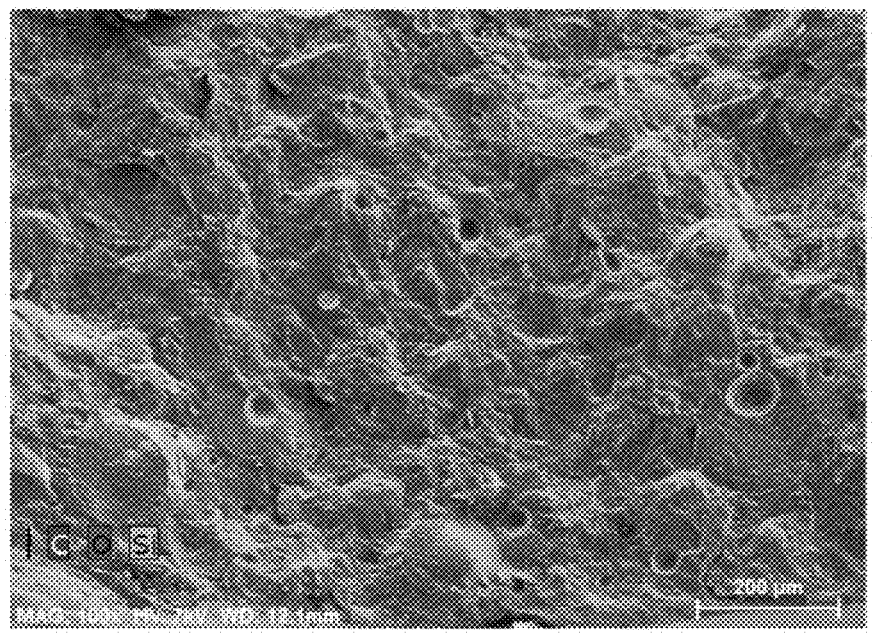
FIGS. 1A and 1B are micrographs of a magnified cross-sectional view of a consumer product composition of the present invention.

The present invention relates to a consumer product composition comprising a non-porous dissolvable solid structure comprising from about 30% to about 95%, by weight of the consumer product composition, of a carrier material, and from about 5% to about 50%, by weight of the consumer product composition, of a hydrophobic conditioning agent disposed within the carrier material of the non-porous dissolvable solid structure. The carrier material comprises a polyethylene glycol material, or mixtures thereof, having a molecular weight of from about 200 to about 50,000. The hydrophobic conditioning agent is selected from the group consisting of silicone materials, organic conditioning oils, hydrocarbon oils, fatty esters, metathesized unsaturated polyol esters, silane-modified oils, and mixtures thereof.

As used herein, consumer product compositions generally encompass beauty care product compositions, and fabric and home care product compositions. Beauty care product compositions generally include product compositions for treating hair, including, bleaching, coloring, dyeing, conditioning, growing, removing, retarding growth, shampooing, styling; deodorants and antiperspirants; personal cleansing; color cosmetics; products, and/or methods relating to treating skin, including application of creams, lotions, and other topically applied products for consumer use; and products and/or methods relating to orally administered materials for enhancing the appearance of hair, skin, and/or nails; and shaving. Fabric and home care product compositions generally include product compositions for treating fabrics, hard surfaces and any other surfaces in the area of fabric and home care, such as car care, dishwashing, fabric conditioning (including softening), laundry detergency, laundry and rinse additive and/or care, hard surface cleaning and/or treatment, and other cleaning for consumer or institutional use.

Suitable consumer product compositions are selected from the group consisting of hand washing product compositions, body wash product compositions, hair shampoo product compositions, hair conditioner product compositions, cosmetic product compositions, hair removal product compositions, laundry rinse additive product compositions, laundry detergent product compositions, fabric softening product compositions, hard surface cleaning product compositions, hand dishwashing product compositions, automatic dishwashing product compositions, and combinations thereof. Preferred consumer product compositions are selected from the group consisting of hair shampoo product compositions, hair conditioner product compositions, laundry detergent product compositions, fabric softening product compositions, and combinations thereof.

Non-Porous Dissolvable Solid Structure

The non-porous dissolvable solid structure of the present invention comprises a carrier material. The carrier material serves to "carry" or "hold" the hydrophobic conditioning agent. The hydrophobic conditioning agent is disposed, as particles, within the carrier material of the non-porous dissolvable solid structure and has a desired mean particle size. The non-porous dissolvable solid structure is capable of dissolving in an aqueous solution to form an aqueous treatment liquor. The dissolution of the non-porous dissolvable solid structure facilitates delivery of the relatively large particles of conditioning agent in the aqueous treatment liquor. The particles of conditioning agent in the aqueous treatment liquor tend to maintain the same mean particle size as the conditioning agent contained in the carrier material of the non-porous dissolvable solid structure prior to dissolution. The conditioning agent can therefore be more effectively deposited and remain on surfaces treated with the aqueous treatment liquor.

With respect to the non-porous dissolvable solid structure, the term "solid" as used herein means that the non-porous dissolvable solid structure has structural rigidity and resistance to change in shape or volume under its own weight (i.e. the weight of the non-porous dissolvable solid structure) at 25° C. As such, the term "solid" includes semi-solids which can change shape or volume under an applied pressure greater than atmospheric pressure. In one aspect, the non-porous dissolvable solid structure is a solid and not a semi-solid.

With respect to the non-porous dissolvable solid structure, the term "non-porous" as used herein means that the non-porous dissolvable solid structure is substantially free of spaces or holes through which liquid or air can pass through the non-porous dissolvable solid structure, such spaces or holes generally having cross-sectional areas of up to about $0.2$ $mm^2$ each (e.g. up to about 500 um diameter dimensions). As such, the term "non-porous dissolvable solid structure" herein does not encompass nonwoven fibrous webs or open-cell foam materials. And as such, the term "non-porous dissolvable solid structure" herein can encompass shapes having larger spaces or holes, such as doughnut-shaped dissolvable solid structures.

The consumer product composition, as a whole, is therefore preferably a non-porous solid consumer product composition (at 25° C.).

Carrier Material

The consumer product composition of the present invention comprises from about 30% to 95%, by weight of the consumer product composition, of a carrier material, within which the hydrophobic conditioning agent is disposed. The carrier material will generally comprise a significant portion of the consumer product composition and serves to maintain the desired mean particle size of the hydrophobic conditioning agent in the consumer product composition. The carrier material comprises a polyethylene glycol material, or mixtures thereof, having a molecular weight of from about 200 to about 50,000.

Polyethylene glycol material, or mixtures thereof, having a molecular weight of from about 200 to about 50,000, is an effective carrier material within which to "set" the mean particle size of the hydrophobic conditioning agent, as its properties facilitate processability in formation of the consumer product composition and effective dissolution of the consumer product composition into aqueous solution, thereby releasing the particles of hydrophobic conditioning agent into the aqueous solution to form an aqueous treatment liquor.

If the consumer product composition of the present invention further comprises filler material, the carrier material level can be decreased accordingly, in which case the consumer product composition can comprise carrier material at a level of at least about 5%, preferably at least about 10%, preferably at least about 20%, preferably at least about 30%, preferably at least about 50%, preferably at least about 60%, preferably at least about 65%, by weight of the consumer product composition. The consumer product composition of the present invention will typically comprise carrier material at a level of less than about 95%, preferably less than about 90%, preferably less than about 85%, by weight of the consumer product composition. Ranges of carrier material are from about 30% to about 95%, from about 50% to about 95%, from about 60% to about 95%, from about 65% to about 95%, or from about 70% to about 90%, by weight of the consumer product composition.

The consumer product composition preferably comprises a ratio of the level of carrier material to the level of hydrophobic conditioning agent of at least about 1:1, preferably from about 1:1 to about 20:1, preferably from about 1:1 to about 10:1, preferably from about 1:1 to about 5:1, preferably from about 1:1 to about 2:1, by weight of the consumer product composition.

The carrier material preferably has a viscosity at 70° C. (as determined according to the VISCOSITY TEST METHOD below), in the range of from about 0.005 to about 350 Pa·s, preferably from about 0.005 to about 100 Pa·s, preferably from about 0.05 to about 50 Pa·s, preferably from about 0.1 to about 15 Pa·s, preferably from about 0.3 to about 15 Pa·s, preferably from about 0.5 to about 15 Pa·s.

The carrier material is generally a solid at ambient temperature (e.g. 25° C.) and can become liquid at elevated temperatures to facilitate incorporation of the hydrophobic conditioning agent in the carrier material at the desired mean particle size. The carrier material preferably becomes liquid (e.g. has a melting point) at a temperature of from about 25° C. to about 120° C., preferably from about 35° C. to about 100° C., preferably from about 40° C. to about 80° C. In preferred aspects, the carrier material is a solid at 25° C. and/or a liquid at 70° C.

The carrier material will typically be selected such that the carrier material portion of the non-porous dissolvable solid structure disperses completely in 25° C. water within a Dispersion Time of less than 60 minutes, preferably less than about 30 minutes, preferably less than about 20 minutes, preferably less than about 10 minutes. In some aspects, such as for a hair conditioning consumer product composition, the carrier material portion of the non-porous dissolvable solid structure completely disperses in 25° C. water within a Dispersion Time of less than about 5 minutes, preferably less than about 2 minutes, preferably less than about 1 minute. Such dispersion can, for instance, be impacted by the nature of the carrier material and/or the size of the consumer product composition. The complete dispersion and associated Dispersion Time is determined according to the DISPERSION TEST METHOD described below.

The carrier material preferably comprises a polyethylene glycol ("PEG") material. The carrier material can comprise a single PEG material or a mixture of different PEG materials (e.g. PEG materials having different average molecular weights). The carrier material can further comprise materials miscible with other carrier materials, e.g. in a liquefied state, such as materials miscible with, e.g. liquefied, polyethylene glycol carrier material.

Polyethylene Glycol Material

Polyethylene glycol ("PEG") materials are preferred carrier materials of the non-porous dissolvable solid structure of the present invention, as PEG materials generally have a relatively low cost, may be formed into many different shapes and sizes, dissolve well in water, and liquefy at elevated temperatures. PEG materials come in various molecular weights. In the consumer product compositions of the present invention, the carrier material comprises a PEG material, or mixtures thereof, having a molecular weight of from about 200 to about 50,000, preferably from about 500 to about 20,000, preferably from about 1,000 to about 15,000, preferably from about 1,500 to about 12,000, alternatively from about 7,000 to about 9,000, alternatively combinations thereof. Suitable carrier materials include PEG material having a molecular weight of about 8,000, PEG material having a molecular weight of about 400, PEG material having a molecular weight of about 20,000, or mixtures thereof. Suitable PEG materials are commercially available from BASF under the trade name PLURIOL, such as PLURIOL E 8000.

As used herein, the molecular weight of the PEG material is determined by the MOLECULAR WEIGHT TEST METHOD described hereinbelow.

The carrier material can comprise a mixture of different PEG materials. Such mixture of PEG materials preferably provides a carrier material having the desired properties of the carrier material as a whole, e.g. viscosity at 70° C., melting point, water solubility, and the like, of the carrier material. In one aspect, the carrier material comprises a PEG material having a molecular weight of about 8,000 and a second PEG material having a molecular weight of about 400.

The consumer product compositions of the present invention comprise at least about 30%, preferably from about 30% to about 95%, preferably from about 50% to about 95%, by weight of the consumer product composition, of a PEG carrier material. Alternatively, the consumer product compositions can comprise from about 80% to about 90%, alternatively from about 85% to about 90%, and alternatively more than about 75%, alternatively from about 70% to about 98%, alternatively from about 80% to about 95%, alternatively combinations thereof and any whole percentages or ranges of whole percentages within any of the aforementioned ranges, of PEG material by weight of the consumer product composition.

PEG materials further include material that might comprise monomers other than ethylene oxide, in particular at low levels. Examples of such monomers include propylene oxide, and other alkylene oxides, glycidyl and other epoxide-containing, formaldehyde, organic alcohols or other polyol monomers. Inclusion of such monomers in the PEG material may be used so long as the PEG material is solid at room temperature.

Hydrophobic Conditioning Agent

The consumer product composition of the present invention comprises from about 5% to about 50%, by weight of the consumer product composition, of a hydrophobic conditioning agent disposed within the carrier material of the non-porous dissolvable solid structure of the consumer product composition. The hydrophobic conditioning agent of the present invention functions to enhance surfaces treated with the consumer product composition to provide improved hand feel benefits (e.g. soft, silky feel), softness benefits, or the like. The term "hydrophobic conditioning agent" as used herein does not encompass perfumes or perfume materials. The hydrophobic conditioning agent is preferably a hydrophobic fiber conditioning agent for treating fibrous surfaces. The hydrophobic conditioning agent is selected from the group consisting of silicones, organic conditioning oils, hydrocarbon oils, fatty esters, metathesized unsaturated polyol esters, silane-modified oils, and mixtures thereof.

The desired mean particle size of the hydrophobic conditioning agent is set and maintained via the carrier material within which the hydrophobic conditioning agent is disposed.

Figure 1B:
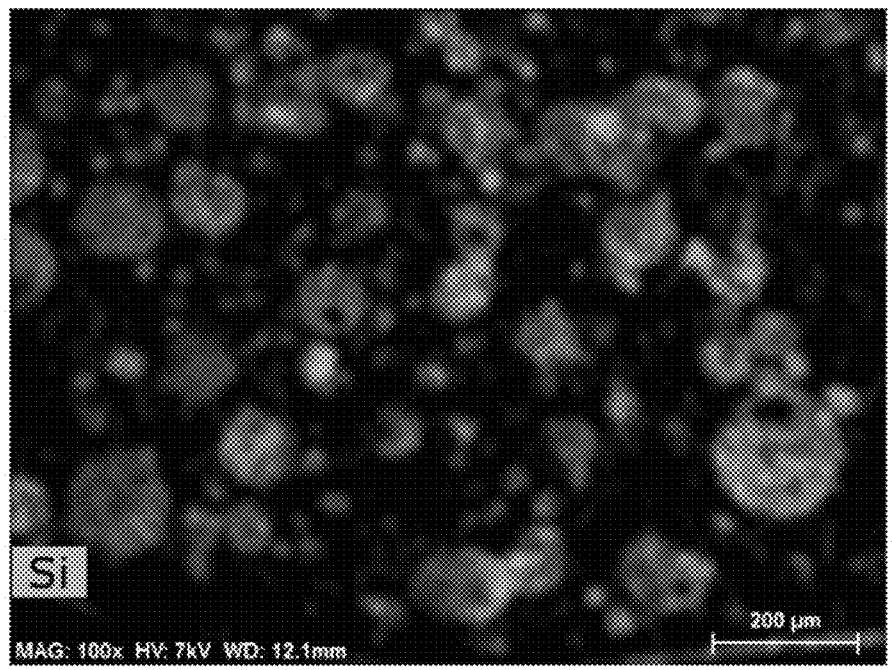

The micrographs in FIGS. 1A and 1B show a magnified cross-sectional view of a consumer product composition, according to Example 6 hereinbelow, containing hydrophobic conditioning agent (terminal aminosilicone available as MAGNASOFT PLUS) disposed within a carrier material (50/50 blend of PEG 8000 and PEG 400) of the non-porous dissolvable solid structure. FIG. 1A highlights the content and location of silicone (MAGNASOFT PLUS) relative to oxygen and carbon in the consumer product composition. FIG. 1B highlights only the content and location of silicone to more clearly illustrate the particles of silicone that are disposed within the carrier material of the non-porous dissolvable solid structure of the consumer product composition.

Hydrophobic conditioning agents include materials which are used to give a particular conditioning benefit (i.e. softening benefit) to hair, skin, and/or fabrics. Suitable conditioning agents include those which deliver one or more benefits relating to shine, softness, comb-ability, antistatic properties, anti-wrinkle properties, wet-handling, fiber damage prevention, manageability, body, and greasiness. The conditioning agents useful in the compositions of the present invention typically comprise a water-insoluble, non-volatile liquid. Suitable conditioning agents for use in the composition are those conditioning agents characterized generally as silicones (e.g., silicone oils, aminosilicones, cationic silicones, silicone gums, high refractive silicones, functionalized silicones, silicone resins, alkyl siloxane polymers, and cationic organopolysiloxanes), organic conditioning oils (e.g., hydrocarbon oils, polyolefins, fatty esters, metathesized unsaturated polyol esters, and silane-modified oils) or combinations thereof, or those conditioning agents which otherwise form liquid, dispersed particles in the carrier material of the non-porous dissolvable solid structure.

The concentration of the conditioning agent in the composition should be sufficient to provide the desired conditioning benefits. Such concentration can vary with the conditioning agent, the conditioning performance desired, the type and concentration of other components, and other like factors such as dosage amount at point of use by the consumer.

The hydrophobic conditioning agent utilized in the present invention will generally have a viscosity at 70° C. (as measured at 70° C. according to the VISCOSITY TEST METHOD below) of at least about 0.01 Pa·s (10 centipoise), preferably from about 0.1 Pa·s (100 centipoise) to about 2000 Pa·s (2,000,000 centipoise), preferably from about 0.1 Pa·s (100 centipoise) to about 150 Pa·s (150,000 centipoise), preferably from about 0.2 Pa·s (200 centipoise) to about 20 Pa·s (20,000 centipoise), preferably from about 0.5 Pa·s (500 centipoise) to about 10 Pa·s (10,000 centipoise).

In preferred aspects, the hydrophobic conditioning agent is liquid at ambient temperature (e.g. 25° C.). The preferred liquid hydrophobic conditioning agent will typically have a viscosity at 25° C. of from about 0.01 Pa·s (10 centipoise), preferably from about 0.1 Pa·s (100 centipoise) to about 2000 Pa·s (2,000,000 centipoise), preferably from about 0.1 Pa·s (100 centipoise) to about 150 Pa·s (150,000 centipoise), preferably from about 0.1 Pa·s (100 centipoise) to about 20 Pa·s (20,000 centipoise), preferably from about 0.5 Pa·s (500 centipoise) to about 15 Pa·s (15,000 centipoise). The viscosity of the hydrophobic conditioning agent at 25° C. is determined according to the VISCOSITY TEST METHOD below, except that the Peltier Plate temperature is set to 25° C. (instead of 70° C.), and the Instrument Procedures and Settings (IPS) "Temperature" settings are 25° C. (instead of 70° C.).

In some aspects, it is believed that if the viscosity of the hydrophobic conditioning agent is too high, upon dissolution of the carrier material, the particles of the hydrophobic conditioning agent in the aqueous treatment liquor may deposit on the target substrate, but may not adequately deform and/or spread over the surface of the substrate, particularly if the substrate is a fibrous substrate such as hair or fabric. If the conditioning agent does not adequately deform and/or spread over the substrate, any conditioning benefit may be incomplete as the conditioning agent may not spread evenly or thoroughly over the substrate. Further, if the disposition of the hydrophobic conditioning agent over the substrate includes regions of high local concentration of the hydrophobic conditioning agent, these regions of high concentration can become highly visible and appear as spots on fabric or as oily clumps on hair. Alternately, if the viscosity of the hydrophobic conditioning agent is too low, the relatively large particles that were maintained by the carrier material in the consumer product may further breakdown in the aqueous treatment liquor, resulting in smaller particles which may not deposit on the target surface as well.

The consumer product composition of the present invention will comprise hydrophobic conditioning agent at a level of at least about 5%, preferably at least about 8%, preferably at least about 12%, by weight of the consumer product composition. The consumer product composition of the present invention will comprise hydrophobic conditioning agent at a level of less than about 50%, preferably less than about 40%, preferably less than about 30%, or preferably less than about 20%, by weight of the consumer product composition. Preferred ranges of hydrophobic conditioning agent are from about 5% to about 50%, from about 5% to about 40%, from about 10% to about 40%, from about 7% to about 35%, from about 10% to about 25%, or from about 15% to about 20%, by weight of the consumer product composition.

Silicones

The conditioning agent of the compositions of the present invention is preferably a water-insoluble silicone conditioning agent. The silicone conditioning agent may comprise volatile silicone, non-volatile silicone, or combinations thereof. Preferred are non-volatile silicone conditioning agents. If volatile silicones are present, it will typically be incidental to their use as a solvent or carrier for commercially available forms of non-volatile silicone material ingredients, such as silicone gums and resins. The silicone conditioning agent particles may comprise a silicone fluid conditioning agent and may also comprise other ingredients, such as a silicone resin to improve silicone fluid deposition efficiency.

Suitable silicones are selected from the group consisting of siloxanes, silicone gums, aminosilicones, terminal aminosilicones, alkyl siloxane polymers, cationic organopolysiloxanes, and mixtures thereof.

The concentration of the silicone conditioning agent ranges from about 5% to about 40%, in one aspect from about 10% to about 40%, in another aspect from about 12% to about 40%, or in another aspect from about 15% to about 30%, by weight of the consumer product composition. Non-limiting examples of suitable silicone conditioning agents are described in U.S. Reissue Pat. No. 34,584, U.S. Pat. Nos. 5,104,646, and 5,106,609.

The hydrophobic conditioning agents of the present invention may comprise one or more silicones including high molecular weight polyalkyl or polyaryl siloxanes and silicone gums; lower molecular weight polydimethyl siloxane fluids; and aminosilicones.

Higher molecular weight silicone compounds useful herein include polyalkyl or polyaryl siloxanes with the following structure:

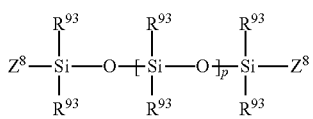

wherein $R^{93}$ is alkyl or aryl, and p is an integer from about 1,300 to about 15,000, more preferably from about 1,600 to about 15,000. $Z^8$ represents groups which block the ends of the silicone chains. The alkyl or aryl groups substituted on the siloxane chain ($R^{93}$) or at the ends of the siloxane chains $Z^8$ can have any structure as long as the resulting silicone remains fluid at room temperature, is neither irritating, toxic nor otherwise harmful, is compatible with the other components of the composition, is chemically stable under normal use and storage conditions, and is capable of being deposited on the target surface. Suitable $Z^8$ groups include hydroxy, methyl, methoxy, ethoxy, propoxy, and aryloxy. The $R^{93}$ groups may represent the same group or different groups. Preferably, the $R^{93}$ groups represent the same group. Suitable $R^{93}$ groups include methyl, ethyl, propyl, phenyl, methylphenyl and phenylmethyl. Other silicone compounds include polydimethylsiloxane, polydiethylsiloxane, and polymethylphenylsiloxane. Commercially available silicone compounds useful herein include, for example, those available from the General Electric Company in their TSF451 series, and those available from Dow Corning in their Dow Corning SH200 series.

The silicone compounds that can be used herein can also include a silicone gum. The term "silicone gum", as used herein, means a polyorganosiloxane material having a viscosity at 25° C. of greater than or equal to 1,000 Pa·s. It is recognized that the silicone gums described herein can also have some overlap with the above-disclosed silicone compounds. This overlap is not intended as a limitation on any of these materials. The "silicone gums" will typically have a molecular weight in excess of about 165,000, generally between about 165,000 and about 1,000,000. Specific examples include polydimethylsiloxane, poly(dimethylsiloxane methylvinylsiloxane) copolymer, poly(dimethylsiloxane diphenylsiloxane methylvinylsiloxane) copolymer and mixtures thereof. Commercially available silicone gums useful herein include, for example, TSE200A and CF330M available from the General Electric Company.

Lower molecular weight silicone compounds useful herein include polyalkyl or polyaryl siloxanes with the following structure:

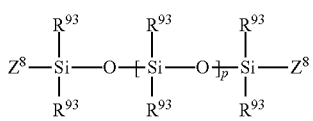

wherein $R^{93}$ is alkyl or aryl, and p is an integer from about 7 to about 850, more preferably from about 7 to about 665. $Z^8$ represents groups which block the ends of the silicone chains. The alkyl or aryl groups substituted on the siloxane chain ($R^{93}$) or at the ends of the siloxane chains $Z^8$ can have any structure as long as the resulting silicone remains fluid at room temperature, is neither irritating, toxic nor otherwise harmful, is compatible with the other components of the composition, is chemically stable under normal use and storage conditions, and is capable of being deposited on the target surface. Suitable $Z^8$ groups include hydroxy, methyl, methoxy, ethoxy, propoxy, and aryloxy. The $R^{93}$ groups may represent the same group or different groups. Preferably, the $R^{93}$ groups represent the same group. Suitable $R^{93}$ groups include methyl, ethyl, propyl, phenyl, methylphenyl and phenylmethyl. Other silicone compounds include polydimethylsiloxane, polydiethylsiloxane, and polymethylphenylsiloxane. Commercially available these silicone compounds useful herein include, for example, those available from the General Electric Company in their TSF451 series, and those available from Dow Corning in their Dow Corning SH200 series.

In one aspect, the hydrophobic conditioning agent of the present invention includes one or more aminosilicones Aminosilicones, as provided herein, are silicones containing at least one primary amine, secondary amine, tertiary amine, or quaternary ammonium group. Preferred aminosilicones may have less than about 1% nitrogen by weight of the aminosilicone, more preferably less than about 0.2%, more preferably still, less than about 0.1%. It should be understood that in some product forms, higher levels of nitrogen are acceptable in accordance with the present invention.

Non-limiting examples of aminosilicones for use in aspects of the subject invention include, but are not limited to, those which conform to the general formula (I):

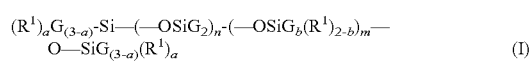

$$(R^1)_a G_{(3-a)}\text{-Si}\text{—}(\text{—OSiG}_2)_n\text{-}(\text{—OSiG}_b(R^1)_{2-b})_m\text{—}$$
$$\text{O}\text{—SiG}_{(3-a)}(R^1)_a \qquad (I)$$

wherein G is hydrogen, phenyl, hydroxy, or $C_1$-$C_8$ alkyl, preferably methyl; a is 0 or an integer having a value from 1 to 3, preferably 1; b is 0, 1, or 2, preferably 1; wherein when a is 0, b is not 2; n is a number from 0 to 1,999; m is an integer from 0 to 1,999; the sum of n and m is a number from 1 to 2,000; a and m are not both 0; $R^1$ is a monovalent radical conforming to the general formula $CqH_{2q}L$, wherein q is an integer having a value from 2 to 8 and L comprises at least one amine group. Preferably L is selected from the following groups: —N($R^2$)$CH_2$—$CH_2$—N($R^2$)$_2$; —N($R^2$)$_2$; —N($R^2$)$^+_3$$A^-$; —N($R^2$)$CH_2$—$CH_2$—$NR^2H_2A^-$; wherein $R^2$ is hydrogen, phenyl, benzyl, or a saturated hydrocarbon radical, preferably an alkyl radical from about $C_1$ to about $C_{20}$; A is a halide ion. Preferably L is —N($R^2$)$CH_2$—$CH_2$—N($R^2$)$_2$, wherein q=3 and $R^2$=H (such a material is available from Momentive Performance Materials Inc. under the tradename MAGNASOFT PLUS).

Some silicones for use herein can include those aminosilicones that correspond to formula (I) wherein m=0, a=1, q=3, G=methyl, n is preferably from about 1500 to about 1700, more preferably about 1600; and L is —N(CH$_3$)$_2$ or —NH$_2$, more preferably —NH$_2$. Other aminosilicones can include those corresponding to formula (I) wherein m=0, a=1, q=3, G=methyl, n is preferably from about 400 to about 600, more preferably about 500; and L is —N(CH$_3$)$_2$ or —NH$_2$, more preferably —NH$_2$. These aminosilicones can be called as terminal aminosilicones, as one or both ends of the silicone chain are terminated by nitrogen containing group.

An exemplary aminosilicone corresponding to formula (I) is the polymer known as "rimethylsilylamodimethicone", which is shown below in formula (II):

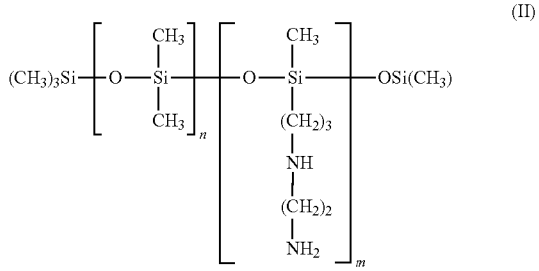

wherein n is a number from 1 to 1,999 and m is a number from 1 to 1,999.

The silicone may also be a terminal aminosilicone. "Terminal aminosilicone" as defined herein means a silicone polymer comprising one or more amino groups at one or both ends of the silicone backbone. In one aspect, the hydrophobic conditioning agent consists of only terminal aminosilicones.

In one aspect, the amino group at the at least one terminus of the silicone backbone of the terminal aminosilicone is selected from the group consisting of: primary amines, secondary amines and tertiary amines. The terminal aminosilicone may conform to Formula III:

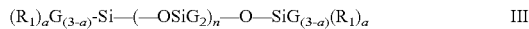

wherein G is hydrogen, phenyl, hydroxy, or $C_1$-$C_8$ alkyl, preferably methyl; a is an integer having a value from 1 to 3, or preferably is 1; n is a number from 0 to 1,999; $R_1$ is a monovalent radical conforming to the general formula $C_qH_{2q}L$, wherein q is an integer having a value from 2 to 8 and L comprises at least one amine group. Preferably L is selected from the following groups: —N($R_2$)$CH_2$—$CH_2$—N($R_2$)$_2$; —N($R_2$)$_2$; —N$^+$($R_2$)$_3$A$^-$; —N($R_2$)$CH_2$—$CH_2$—N$^+$$R_2H_2A^-$; wherein $R_2$ is hydrogen, phenyl, benzyl, or a saturated hydrocarbon radical; A is a halide ion. In an aspect, $R_2$ is an alkyl radical having from 1 to 20 carbon atoms, or from 2 to 18 carbon atoms, or from 4 to 12 carbon atoms.

A suitable terminal aminosilicone corresponding to Formula III has a=1, q=3, G=methyl, n is from about 1000 to about 2500, alternatively from about 1500 to about 1700; and L is —N($CH_3$)$_2$. In an aspect, $R_2$ is an alkyl radical having from 1 to 20 carbon atoms, or from 2 to 18 carbon atoms, or from 4 to 12 carbon atoms. In an aspect, the terminal aminosilicone is selected from the group consisting of bis-aminomethyl dimethicone, bis-aminoethyl dimethicone, bis-aminopropyl dimethicone, bis-aminobutyl dimethicone, and mixtures thereof.

Suitable silicones further include aminopropyl terminated polydimethylsiloxane (e.g. having a viscosity of 4,000-6,000 cSt (4-6 Pa·s); available under the tradename DMS-A35 from Gelest, Inc.), polydimethylsiloxane, trimethylsiloxy terminated (e.g. having a viscosity of 5,000 cSt (5 Pa·s); available under the tradename DMS-T35 from Gelest, Inc.), polydimethylsiloxane, trimethylsiloxy terminated (e.g. having a viscosity of 1,000 cSt (1 Pa·s); available under the tradename DMS-T31 from Gelest, Inc.), aminopropyl terminated polydimethylsiloxane (e.g. having a viscosity of 900-1,100 cSt (0.9-1.1 Pa·s); available under the tradename DMS-A31 from Gelest, Inc.), polydimethylsiloxane, trimethylsiloxy terminated (e.g. having a viscosity of 50 cSt (0.05 Pa·s); available under the tradename DMS-T15 from Gelest, Inc), aminopropyl terminated polydimethylsiloxane (e.g. having a viscosity of 50-60 cSt (0.05-0.06 Pa·s); available under the tradename DMS-A15 from Gelest, Inc.), bis-aminopropyl dimethicone (e.g. having a viscosity of 10,220 cSt (10.2 Pa·s); available from Momentive Performance Materials Inc.), and mixtures thereof.

Alkyl Siloxane Polymer

Suitable conditioning agents as benefit agents of the hydrophobic coating further include alkyl siloxane polymers, as described in detail in US 2011/0243874 A1, US 2011/0243875 A1, US 2011/0240065 A1, US 2011/0243878A1, US 2011/0243871 A1, and US 2011/0243876 A1.

Cationic Organopolysiloxanes

Suitable conditioning agents as benefit agents of the hydrophobic coating further include cationic organopolysiloxanes, as described in detail in US 2014/0030206 A1, WO 2014/018985 A1, WO 2014/018986 A1, WO 2014/018987 A1, WO 2014/018988 A1, and WO 2014/018989 A1.

Organic Conditioning Oils

The hydrophobic conditioning agent of the compositions of the present invention may also comprise at least one organic conditioning oil as the conditioning agent, either alone or in combination with other conditioning agents, such as the silicones. Suitable organic conditioning oils include hydrocarbon oils, polyolefins, fatty esters, methathesized unsaturated polyol esters, or silane-modified oils.

Hydrocarbon Oils

Suitable organic conditioning oils for use as conditioning agents in the compositions of the present invention include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils preferably are from about $C_{12}$ to about $C_{22}$.

Specific non-limiting examples of these hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, polybutene, polyisobutylene, polydecene, and mixtures thereof. Branched-chain isomers of these compounds, as well as of higher chain length hydrocarbons, can also be used, examples of which include highly branched, saturated or unsaturated, alkanes such as the permethyl-substituted isomers, e.g., the permethyl-substituted isomers of hexadecane and eicosane, such as 2, 2, 4, 4, 6, 6, 8, 8-dimethyl-10-methylundecane and 2, 2, 4, 4, 6, 6-dimethyl-8-methylnonane, available from Permethyl Corporation. Hydrocarbon polymers such as polybutene and polydecene. A preferred hydrocarbon polymer is polybutene, such as the copolymer of isobutylene and butene. A commercially available material of this type is L-14 polybutene from Amoco Chemical Corporation. Another preferred hydrocarbon polymer is polyisobutylene, a non-limiting example being polyisobutylene having a number average molecular weight of 1,000 and commercially available from EVONIK Industries AG under the trade name REWOPAL PIB 1000.

Polyolefins

Organic conditioning oils for use in the compositions of the present invention can also include liquid polyolefins, liquid poly-α-olefins, hydrogenated liquid poly-α-olefins, and the like. Polyolefins for use herein are prepared by polymerization of $C_4$ to about $C_{14}$ olefenic monomers.

Non-limiting examples of olefenic monomers for use in preparing the polyolefin liquids herein include ethylene, propylene, butene (including isobutene), pentene, hexene, octene, decene, dodecene, tetradecene, branched chain isomers such as 4-methyl-1-pentene, and mixtures thereof. Also suitable for preparing the polyolefin liquids are olefin-containing refinery feedstocks or effluents. Hydrogenated α-olefin monomers include, but are not limited to: 1-hexene to 1-hexadecenes, 1-octene to 1-tetradecene, and mixtures thereof.

Fatty Esters

Other suitable organic conditioning oils for use as conditioning agents in the compositions of the present invention include, but are not limited to, fatty esters having at least 10 carbon atoms. These fatty esters include esters with hydrocarbyl chains derived from fatty acids or alcohols (e.g. mono-esters, polyhydric alcohol esters, and di- and tri-carboxylic acid esters). The hydrocarbyl radicals of the fatty esters hereof may include or have covalently bonded thereto other compatible functionalities, such as amides and alkoxy moieties (e.g., ethoxy or ether linkages, etc.).

Specific examples of fatty esters include, but are not limited to: isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate.

Other fatty esters suitable for use in the compositions of the present invention are mono-carboxylic acid esters of the general formula R'COOR, wherein R' and R are alkyl or alkenyl radicals, and the sum of carbon atoms in R and R is at least 10, preferably at least 22.

Still other fatty esters suitable for use in the compositions of the present invention are di- and tri-alkyl and alkenyl esters of carboxylic acids, such as esters of $C_4$ to $C_8$ dicarboxylic acids (e.g. $C_1$ to $C_{22}$ esters, preferably $C_1$ to $C_6$, of succinic acid, glutaric acid, and adipic acid). Specific non-limiting examples of di- and tri-alkyl and alkenyl esters of carboxylic acids include isocetyl stearyol stearate, diisopropyl adipate, and tristearyl citrate.

Other fatty esters suitable for use in the compositions of the present invention are those known as polyhydric alcohol esters. Such polyhydric alcohol esters include alkylene glycol esters, such as ethylene glycol mono- and di-fatty acids, diethylene glycol mono- and di-fatty acid esters, polyethylene glycol mono- and di-fatty acid esters, propylene glycol mono- and di-fatty acid esters, polypropylene glycol monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

Still other fatty esters suitable for use in the compositions of the present invention are glycerides, including, but not limited to, mono-, di-, and tri-glycerides, preferably di- and tri-glycerides, more preferably triglycerides. For use in the compositions described herein, the glycerides are preferably the mono-, di-, and tri-esters of glycerol and long chain carboxylic acids, such as $C_{10}$ to $C_{22}$ carboxylic acids. A variety of these types of materials can be obtained from vegetable and animal fats and oils, such as castor oil, safflower oil, cottonseed oil, corn oil, olive oil, cod liver oil, almond oil, avocado oil, palm oil, sesame oil, lanolin and soybean oil. Synthetic oils include, but are not limited to, triolein and tristearin glyceryl dilaurate.

Other fatty esters suitable for use in the compositions of the present invention are water insoluble synthetic fatty esters. Some preferred synthetic esters conform to the general Formula (IX):

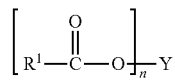

wherein $R^1$ is a $C_7$ to $C_9$ alkyl, alkenyl, hydroxyalkyl or hydroxyalkenyl group, preferably a saturated alkyl group, more preferably a saturated, linear, alkyl group; n is a positive integer having a value from 2 to 4, preferably 3; and Y is an alkyl, alkenyl, hydroxy or carboxy substituted alkyl or alkenyl, having from about 2 to about 20 carbon atoms, preferably from about 3 to about 14 carbon atoms. Other preferred synthetic esters conform to the general Formula (X):

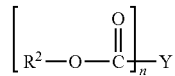

wherein $R^2$ is a $C_8$ to $C_{10}$ alkyl, alkenyl, hydroxyalkyl or hydroxyalkenyl group; preferably a saturated alkyl group, more preferably a saturated, linear, alkyl group; n and Y are as defined above in Formula (X).

Specific non-limiting examples of suitable synthetic fatty esters for use in the compositions of the present invention include: P-43 ($C_8$-$C_{10}$ triester of trimethylolpropane), MCP-684 (tetraester of 3,3 diethanol-1,5 pentadiol), MCP 121 ($C_8$-$C_{10}$ diester of adipic acid), all of which are available from Mobil Chemical Company.

Metathesized Unsaturated Polyol Esters

Other suitable organic conditioning oils as conditioning agents include metathesized unsaturated polyol esters. Exemplary metathesized unsaturated polyol esters and their starting materials are set forth in US 2009/0220443 A1. A metathesized unsaturated polyol ester refers to the product obtained when one or more unsaturated polyol ester ingredient(s) are subjected to a metathesis reaction. Metathesis is a catalytic reaction that involves the interchange of alkylidene units among compounds containing one or more double bonds (i.e., olefinic compounds) via the formation and cleavage of the carbon-carbon double bonds. Metathesis may occur between two of the same molecules (often referred to as self-metathesis) and/or it may occur between two different molecules (often referred to as cross-metathesis).

Silane-Modified Oils

Other suitable organic conditioning oils as conditioning agents include silane-modified oils. In general, suitable silane-modified oils comprise a hydrocarbon chain selected from the group consisting of saturated oil, unsaturated oil, and mixtures thereof; and a hydrolysable silyl group covalently bonded to the hydrocarbon chain. Suitable silane-modified oils are described in detail in U.S. Application Ser. No. 61/821,818, filed May 10, 2013.

Other Conditioning Agents

Also suitable for use in the compositions herein are the conditioning agents described by the Procter & Gamble Company in U.S. Pat. Nos. 5,674,478, and 5,750,122. Also suitable for use herein are those conditioning agents described in U.S. Pat. No. 4,529,586 (Clairol), U.S. Pat. No.

4,507,280 (Clairol), U.S. Pat. No. 4,663,158 (Clairol), U.S. Pat. No. 4,197,865 (L'Oreal), U.S. Pat. No. 4,217,914 (L'Oreal), U.S. Pat. No. 4,381,919 (L'Oreal), and U.S. Pat. No. 4,422,853 (L'Oreal).

Filler Materials

The consumer product composition can optionally further comprise filler materials, which are materials (other than hydrophobic conditioning agents) that are not miscible in the, e.g. liquefied, carrier material. Preferred filler materials include inorganic salts (e.g. sodium chloride), carbohydrates (such as sugars, starches, celluloses, and the like), clays, metal oxides (e.g. $TiO_2$), zeolites, silicas, urea, and the like.

The filler material can be dispersed within the carrier material.

The consumer product composition preferably comprises less than about 5%, preferably less than about 3%, preferably less than about 1%, by weight of the consumer product composition, of water. The consumer product composition is preferably free of water (i.e. anhydrous).

The consumer product composition preferably comprises less than about 5%, preferably less than about 3%, preferably less than about 1%, by weight of the consumer product composition, of detersive surfactant and/or cleansing surfactant. The consumer product composition is preferably free of detersive surfactant and/or cleansing surfactant.

Loading

The consumer product composition of the present invention comprise hydrophobic conditioning agent in an amount of at least about 5%, preferably at least about 10%, preferably at least about 15%, by weight of the consumer product composition.

Figure 2:
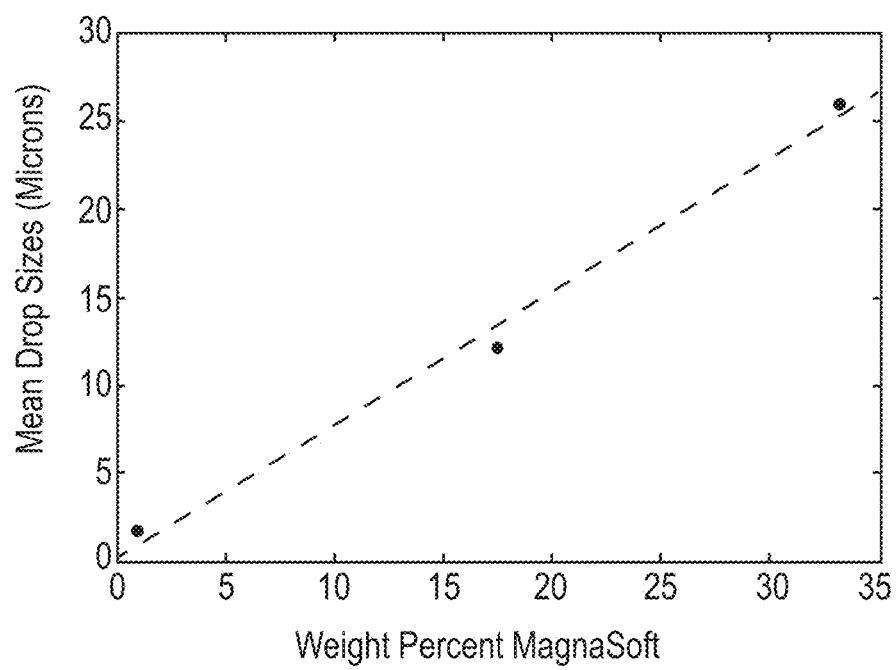
FIG. 2 is a plot of mean particle size versus weight percent of hydrophobic conditioning agent.

The amount of hydrophobic conditioning agent disposed in the carrier material in the non-porous dissolvable solid substrate can tend to have an affect on the mean particle size of the hydrophobic conditioning agent in the consumer product composition. In general, the greater the amount of hydrophobic conditioning agent in the non-porous dissolvable solid structure, the greater the mean particle size of the hydrophobic conditioning agent disposed within the carrier material of the non-porous dissolvable solid structure of the consumer product composition. This phenomenon is demonstrated by the data presented in FIG. 2, which is a plot of mean particle size (in microns) versus weight percent of hydrophobic conditioning agent (terminal aminosilicone available as MAGNASOFT PLUS), by weight of the consumer product composition.

As illustrated below by the data presented in FIG. 6, the consumer product compositions of the present invention, especially those for conditioning fabrics in a laundry process, will comprise at least about 5%, by weight of the consumer product composition, of hydrophobic conditioning agent in order to achieve consumer-noticeable levels of fabric conditioning performance.

It has also been found that the level of hydrophobic conditioning agent in the consumer product composition determines the amount of consumer product required at point of use by the consumer to derive the desired degree of conditioning benefit. Specifically, at higher levels of loading, less consumer product composition is required per use.

Form of Consumer Product Composition

The consumer product composition of the present invention is preferably provided in the form of a plurality of beads. The size of the beads is tailored so that they are large enough to be easily handled yet small enough to dissolve in the context of the use environment. For example, use of the consumer product in a clothes washing machine may require that the carrier material of the product composition dissolve in the course of a few minutes and in the context of a variety of water temperatures. Separately, use in a personal care context may require that the carrier material of the product dissolve in a fewer number of minutes when wetted and rubbed between the palms of the hands.

The physical size of the beads may be expressed as the average of the maximum cross-sectional dimension of the plurality of beads.

The maximum cross-sectional dimension of any single bead within the plurality of beads is taken as the length of the longest linear dimension that can be inscribed entirely within the outer perimeter of the single bead. The average maximum cross-sectional dimension of the plurality of beads may be taken as the average of the longest linear dimension that can be inscribed entirely within the single bead, across all the beads within the plurality of beads. It would be appreciated by one of ordinary skill in the art that this average may also be reflected by taking the average across a statistically relevant sample of beads from the plurality of beads.

The plurality of beads preferably have an average maximum cross-sectional dimension of from about 0.05 to about 50 mm, preferably from about 0.3 to about 10 mm, preferably from about 0.5 to about 5 mm, preferably from about 1 to about 3 mm. It is recognized that the average maximum cross-sectional dimension of the plurality of beads will be greater (preferably at least two times greater) than the mean particle size of the hydrophobic conditioning agent within the carrier material of the non-porous dissolvable solid structure.

The beads of the consumer product composition may take any shape. For example the shape may be everywhere convex (e.g. a sphere) or may have areas of convexity. The shape may include any basic three-dimensional shape, such as spheres, hemispheres, oblate spheres, spheroids, discs, plates, cones, truncated cones, prisms, cylinders, pyramids, noodles, rectangles, doughnuts, toroids, and the like. The shape may be formed to resemble recognizable shapes such as a heart, star, shamrock, pretzel, "smiley face" and the like. The shape may include recognizable imagery such as icons and logos including logos representative of product brands. The shapes may be uniform shapes, a combination of different shapes, or generally random shapes (such as prills).

The physical shape of the bead can be expressed in terms of an aspect ratio of the bead. The aspect ratio of a bead is the ratio of maximum cross-sectional dimension of the bead to the longest dimension which is perpendicular to the maximum cross-sectional dimension and entirely within the outer perimeter of the bead. The aspect ratio of a single bead, or the average aspect ratio of a plurality of beads, is preferably from about 1:1 to about 1000:1, preferably from about 1:1 to about 100:1, preferably from about 1:1 to about 10:1, preferably from about 1:1 to about 2:1.

Mean Particle Size of Hydrophobic Conditioning Agent

The hydrophobic conditioning agent is typically disposed within the carrier material as substantially discrete particles with relatively large mean particle size. Without being bound by theory, it is believed that the relatively large mean particle size of hydrophobic conditioning agent facilitates deposition of the hydrophobic conditioning agent on the target surface. The desired mean particle size of the hydrophobic conditioning agent can be "set" in the carrier material of the non-porous dissolvable solid structure upon solidification of a melt composition which comprises a mixture of liquefied hydrophobic conditioning agent and liquefied carrier material. In making the consumer product composition, the carrier material is liquefied prior to mixing the hydrophobic conditioning agent within it, for example by heating the carrier material to a temperature above its melting point (e.g. 70° C.).

The mean particle size of the hydrophobic conditioning agent disposed in the carrier material of the non-porous dissolvable solid structure of the consumer product composition is typically from about 2 μm to about 2000 μm. The mean particle size of the hydrophobic conditioning agent disposed in the non-porous dissolvable solid structure is determined according to the MEAN PARTICLE SIZE method described hereinbelow. As used herein, the mean particle size of the hydrophobic conditioning agent reflects the mean particle diameter as measured according to the MEAN PARTICLE SIZE method.

The optimal mean particle size of the hydrophobic conditioning agent may depend upon the intended use of the consumer product composition. For instance, a fabric softening product composition for conditioning fabrics in a laundry process will preferably contain a hydrophobic conditioning agent having a mean particle size of from about 2 μm to about 500 μm, more preferably from about 2 μm to about 120 μm, more preferably from about 2 μm to about 70 μm; whereas a hair conditioning product composition for conditioning hair in a hair washing process will preferably contain a hydrophobic conditioning agent having a mean particle size of from about 10 μm to about 2,000 μm. Since the consumer product composition is in a solid, non-porous form, the particle size of the hydrophobic conditioning agent will generally remain constant during packaging, shipping and storage of the consumer product composition.

Process of Making the Consumer Product Composition

In general, a process of making the consumer product composition of the present invention comprising a non-porous dissolvable solid structure can include pastillation processes, prilling processes, molding processes, extrusion processes, and the like.

Such processes of making a consumer product composition comprising a non-porous dissolvable solid structure typically comprise the steps of
  providing a carrier material (preferably having a melting point of greater than 25° C.);
  heating the carrier material (preferably to a temperature greater than the melting point of the carrier material), mixing a hydrophobic conditioning agent with the heated carrier material to form a melt composition; and
  cooling the melt composition (preferably to a temperature below the melting point of the carrier material) to form the non-porous dissolvable solid structure of the consumer product composition.

A pastillation process for making the consumer product composition of the present invention generally comprises the steps recited above, wherein the step of cooling the melt composition comprises dispensing the melt composition drop-wise onto a cooling surface (i.e. a surface that is cooled relative to ambient temperature (e.g. 25° C.)).

A prilling process for making the consumer product composition of the present invention generally comprises the steps recited above, wherein the step of cooling the melt composition comprises dispensing the melt composition drop-wise into a cooling atmosphere (i.e. a controlled atmosphere in which the air is cooled relative ambient temperature (e.g. 25° C.)).

A molding process for making the consumer product composition of the present invention generally comprises the steps recited above, wherein the step of cooling the melt composition comprises dispensing the melt composition into a mold and further comprising the step of cooling the melt composition in the mold to form the non-porous dissolvable solid structure of the consumer product composition prior to releasing the consumer product composition from the mold.

In certain aspects, it can be preferred that the step of mixing the hydrophobic conditioning agent with the heated carrier material to form a melt composition, provides a Modified Capillary Number of less than about 10, preferably less than about 2, preferably less than about 1, with respect to the melt composition.

A suitable process for making a consumer product composition of the present invention, preferably in the form of a plurality of beads, is described in U.S. Pat. No. 7,867,986.

The amount of shear imparted to the melt composition during the process of making the consumer product composition can have an impact on the mean particle size of the hydrophobic conditioning agent in the resulting consumer product composition. E.g., the mean particle size of the hydrophobic conditioning agent tends to increase as the shear rate is decreased.

Viscosity Ratio

In certain aspects, achieving the relatively large mean particle size of the hydrophobic conditioning agent in the non-porous dissolvable solid structure of the consumer product composition can be impacted by the relative viscosities of the liquefied carrier material composition and the liquid/liquefied hydrophobic conditioning agent (e.g. in the melt composition). It is believed that the higher the viscosity of the liquefied carrier material, the greater the ability of the liquefied carrier material to transfer energy to the dispersed hydrophobic conditioning agent, thereby the greater the tendency for the hydrophobic conditioning agent to form smaller particles. Further, it is believed that the higher the viscosity of the hydrophobic benefit agent (e.g. during manufacture), the greater the ability of the hydrophobic conditioning agent to resist being broken up, thereby the greater the tendency for the hydrophobic conditioning agent to form larger particles. As such, at elevated temperatures in which the carrier material and hydrophobic conditioning agent are both liquid, the viscosity ratio of the viscosity of the hydrophobic conditioning agent to the viscosity of the liquefied carrier material preferably falls within certain ranges to facilitate formation of relatively large mean particle size of hydrophobic conditioning agent in the non-porous dissolvable solid structure of the consumer product composition.

Preferably the ratio of the viscosity of said hydrophobic conditioning agent at 70° C. to the viscosity of said carrier material at 70° C. is from about 1000:1 to about 1:1000, preferably from about 100:1 to about 1:100, preferably from about 10:1 to about 1:10, preferably from about 5:1 to about 1:5.

Modified Capillary Number ($C_m$)

In some aspects, the relatively large mean particle size of the hydrophobic conditioning agent disposed within the carrier material can be facilitated by appropriately selecting materials to provide a Modified Capillary Number (see below) of the system within certain ranges when in the form of a melt composition (e.g. during the process of making the consumer product composition). The hydrophobic conditioning agent of the consumer product composition tends to constitute a dispersed hydrophobic portion (e.g. as particles) within the carrier material, both during manufacture—when the carrier material is in the form of a melt composition (e.g. at elevated temperature)—and in the finished form of the consumer product composition—when the carrier material is a solid (e.g. at 25° C.). It is further believed that the mean particle size of the hydrophobic conditioning agent in the melt composition is similar to that in the finished consumer product composition and that any substantial changes in the mean particle size can be prevented by ensuring sufficiently prompt cooling of the melt composition, effectively "setting" the mean particle size of hydrophobic conditioning agent in the finished consumer product composition.

The Capillary Number provided with respect to the melt composition reflects the ability of the system conditions—including shear rate, viscosity, and interfacial tension—to form particles of the hydrophobic conditioning agent of a given size. For example, if the shear rate is large enough, then the force attempts to pull or stretch particles of the hydrophobic conditioning agent. If stretched far enough, the particles of hydrophobic conditioning agent will break into smaller particles. At the same time, the particles of hydrophobic conditioning agent try to resist stretching through the interfacial tension between the hydrophobic conditioning agent and the liquefied carrier material of the melt composition (as determined by the INTERFACIAL TENSION TEST METHOD described herein below).

The traditional Capillary Number is defined by the following equation:

$$Ca = \frac{r\mu\dot{\upsilon}}{\gamma}$$

wherein:
Ca is the Capillary Number (unitless);
r is the mean particle size of the hydrophobic conditioning agent (in meters) as measured by the PARTICLE SIZE TEST METHOD divided by 2 (thereby representing the mean radius, rather than mean diameter);
$\dot{\upsilon}$ is the Shear Rate (in $s^{-1}$), which is calculated as indicated below;
$\gamma$ is the Interfacial Tension (in $N \cdot m^{-1}$) between the liquefied carrier and liquefied hydrophobic conditioning agent as measured by the INTERFACIAL TENSION TEST METHOD; and
$\mu$ is the viscosity (in Pa·s) of the liquefied carrier material at 70° C. as measured by the VISCOSITY TEST METHOD.

It has further been found that melt compositions from which consumer product compositions of the present invention are made may deviate from the above traditional Capillary Number equation when relatively high weight fractions of the hydrophobic conditioning agent are used (e.g. greater than 0.05 or 5%). Specifically, whereas melt compositions comprising approximately 1% (by weight of the consumer product composition) of the hydrophobic conditioning agent adhere well to the Capillary Number equation as depicted above, melt compositions comprising substantially greater than about 5% hydrophobic conditioning agent may exhibit relatively larger mean particle sizes than predicted by the traditional Capillary Number. It is believed that these relatively larger mean particle sizes may result from the additional effect of coalescence of the particles that further competes with the shear and interfacial tension forces noted above.

As the consumer product composition of the present invention preferably comprises greater than 5% of the hydrophobic conditioning agent, a Modified Capillary Number is preferably used to describe the melt compositions from which consumer product compositions of the present invention are made.

The coalescence effects at higher weight fractions of the hydrophobic conditioning agent can be accounted by a Modified Capillary Number, $C_m$.

The Modified Capillary Number is defined by the following equation:

$$Cm = \frac{[R - S(Wf - 0.01)]\mu\dot{\upsilon}}{\gamma}$$

wherein:
$C_m$ is the Modified Capillary Number (unitless);
S is a constant equal to $3.22 \times 10^{-5}$ (meters);
$W_f$ is the weight fraction (unitless) of the hydrophobic conditioning agent in the melt composition comprising liquefied carrier material and hydrophobic conditioning agent;
R is the mean particle size of the hydrophobic conditioning agent (in meters) as measured by the PARTICLE SIZE TEST METHOD divided by 2 (thereby representing the mean radius, rather than mean diameter);
$\dot{\upsilon}$ is the Shear Rate (in $s^{-1}$), which is calculated as indicated below;
$\gamma$ is the Interfacial Tension (in $N \cdot m^{-1}$) between the liquefied carrier and liquefied hydrophobic conditioning agent as measured by the INTERFACIAL TENSION TEST METHOD; and
$\mu$ is the viscosity (in Pa·s) of the liquefied carrier material at 70° C. as measured by the VISCOSITY TEST METHOD.

With respect to determination of the Modified Capillary Number above, the value to be used for Shear Rate in the Modified Capillary Number equation is calculated based on the following method.

An otherwise-identical consumer product composition is prepared using 1% (by weight of the consumer product composition) of hydrophobic conditioning agent, with the carrier material level adjusted to compensate for the reduced level of hydrophobic conditioning agent (i.e. QS the carrier material). The mean particle size, viscosity and interfacial tension of this 1% consumer product composition is determined (per the methods herein) and the Shear Rate is calculated by using the traditional Capillary Number equation above, with the traditional Capillary Number assigned a value of 0.5 (thereby solving for Shear Rate $\dot{\upsilon}$ (in $s^{-1}$)). Note that the viscosity and interfacial tension measurements are independent of the weight fraction of the components, and that the same values of these parameters apply to both the traditional Capillary Number and the Modified Capillary Number equations above.

Having determined the Shear Rate $\dot{\upsilon}$ (in $s^{-1}$) above by means of the 1% hydrophobic condition agent consumer product composition, the Modified Capillary Number for a consumer product composition comprising greater than 5% hydrophobic condition agent are calculated using the same Shear Rate $\dot{\upsilon}$ value (in $s^{-1}$).

Method of Forming Aqueous Treatment Liquor

The present invention further encompasses a method of forming an aqueous treatment liquor by dissolving the consumer product composition of the present invention. The aqueous treatment liquor can be, for example, an aqueous laundry treatment liquor formed in a washing machine or hand-washing vessel, an aqueous hair treatment liquor formed by a consumer in the shower, an aqueous body treatment liquor formed by a consumer in the shower, an aqueous skin treatment liquor, and the like.

In most applications, the size of the particles of hydrophobic conditioning agent in the non-porous dissolvable solid structure is maintained as the non-porous dissolvable solid structure dissolves and the particles of hydrophobic conditioning agent are released during use. Not wishing to be bound by theory, it is believed that the viscosity of the aqueous treatment liquor relative to the hydrophobic conditioning agent is such that the modest shear in many environments (such as a washing machine) are insufficient to break the particles into yet smaller particles, as long as the viscosity of the hydrophobic conditioning agent is sufficiently high.

The method generally comprises the steps of providing a consumer product composition of the present invention, providing an aqueous solution, and dissolving the consumer product composition in the aqueous solution. As the method steps are carried out, the dissolvable structure of the consumer product composition begins to dissolve in the aqueous solution. As the dissolvable structure dissolves away, the particles of hydrophobic conditioning agent disposed within the carrier material of the non-porous dissolvable solid structure of the consumer product composition are dispersed into the aqueous solution, and tend to maintain their mean particle size in the formed aqueous treatment liquor. It is the resulting relatively large particles of hydrophobic conditioning agent in the aqueous treatment liquor that result in significant improvements in providing the desired benefits to the consumer of the consumer product composition, such as hair conditioning, skin conditioning, or fabric softening.

Figure 3A:
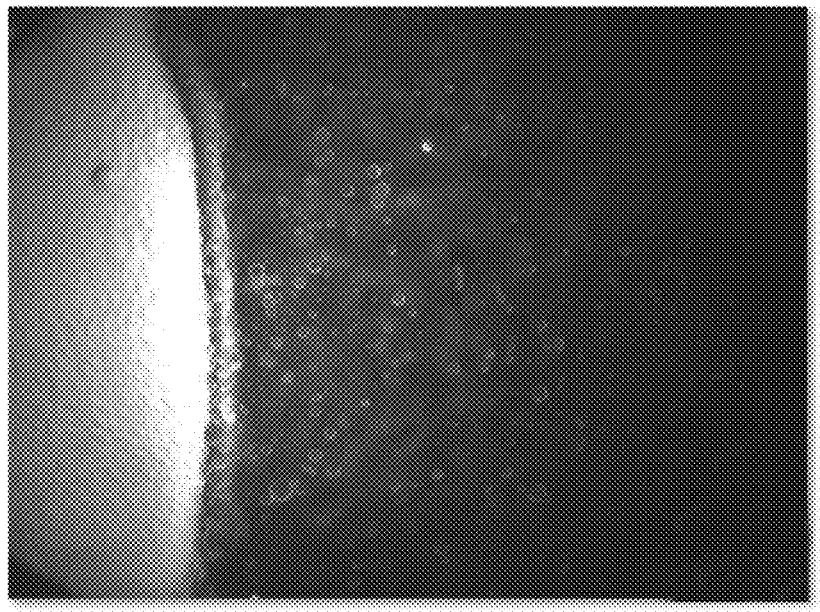
FIGS. 3A and 3B are micrographs of a consumer product composition of the present invention being dissolved in water to form an aqueous treatment liquor.
Figure 3B:
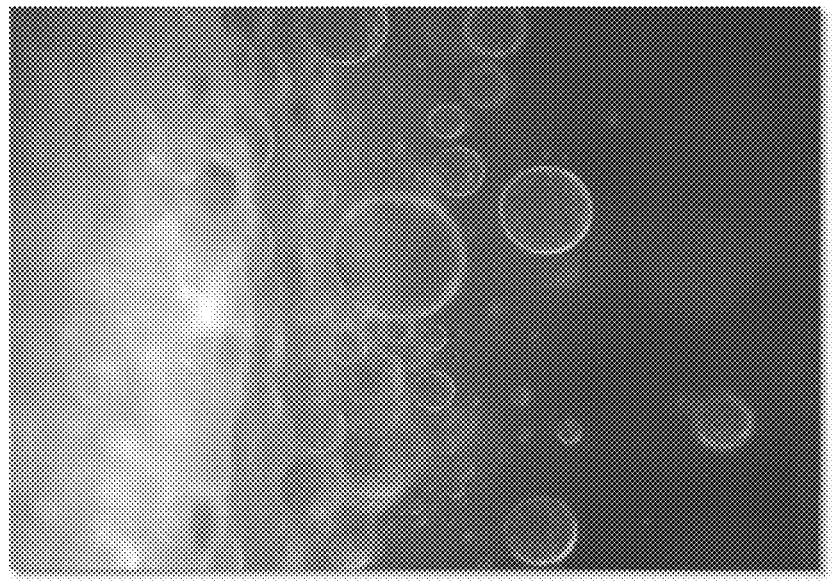

The release of particles of hydrophobic conditioning agent from the dissolvable solid structure of the consumer product composition into the aqueous solution is illustrated in the micrographs of FIGS. 3A and 3B. As shown in FIG. 3A, many particles of hydrophobic conditioning agent are dispersed into aqueous solution from the consumer product composition and tend to maintain their mean particle size in aqueous solution as the particles drift away from the dissolving consumer product composition. The higher-magnification view of FIG. 3B illustrates that even under very concentrated conditions, the particles of hydrophobic conditioning agent do not spread or wet the surface of the consumer product composition as they disperse into aqueous solution. The particles also do not coalesce or aggregate under these flow conditions. As such, the "setting" of the appropriate mean particle size of hydrophobic conditioning agent within the carrier material of the non-porous dissolvable solid structure of the consumer product composition of the present invention is important with respect ultimately forming an aqueous treatment liquor having the desired particle size of hydrophobic conditioning agent to facilitate enhanced deposition and improved conditioning of the surfaces treated.

In forming the aqueous treatment liquor by dissolving the dissolvable structure of the consumer product composition, the method preferably further comprises the step of agitating the aqueous treatment liquor. The agitation of the aqueous treatment liquor can be important, especially in a hair washing or conditioning context, to further facilitate contact between the target surface and the relatively large particles of hydrophobic conditioning agent in the aqueous treatment liquor. The agitation can be accomplished by mechanically manipulating (e.g. by machine or by hand) the aqueous treatment liquor (e.g. agitation), preferably during dissolution of the non-porous dissolvable solid structure.

In one aspect of the present invention, a method of treating a surface comprises the steps of:
providing a consumer product composition according to the present invention;
providing an aqueous solution;
dissolving the consumer product composition in the aqueous solution to form an aqueous treatment liquor; and
contacting the surface with the aqueous treatment liquor.

Test Methods

The following test methods are conducted on samples that have been conditioned, for a minimum of 24 hours prior to testing, in a conditioned room at a temperature of 23° C.±2.0° C. and a relative humidity of 45%±10%. Except where noted, all tests are conducted under the same environmental conditions and in such conditioned room. Except where noted, all quantities are given on a weight basis. Except where noted all water used is laboratory-grade deionized (DI) water. Except where noted, at least three samples are measured for any given material being tested and the results from those three (or more) replicates are averaged to give the final reported value for that material, for that test.

Viscosity Test Method

The viscosity of a component of the consumer product composition, e.g. a hydrophobic conditioning agent or carrier material, is determined as follows.

For a given component, the viscosity reported is the viscosity value as measured by the following method, which generally represents the infinite-shear viscosity (or infinite-rate viscosity) of the component. Viscosity measurements are made with a TA Discovery HR-2 Hybrid Rheometer (TA Instruments, New Castle, Del., U.S.A.), and accompanying TRIOS software version 3.0.2.3156. The instrument is outfitted with a 40 mm stainless steel Parallel Plate (TA Instruments, cat. #511400.901), Peltier plate (TA Instruments cat. #533230.901), and Solvent Trap Cover (TA Instruments, cat. #511400.901). The calibration is done in accordance with manufacturer recommendations. A refrigerated, circulating water bath set to 25° C. is attached to the Peltier plate. The Peltier Plate temperature is set to 70° C. The temperature is monitored within the Control Panel until the instrument reaches the set temperature, then an additional 5 minutes is allowed to elapse to ensure equilibration before loading sample material onto the Peltier plate.

To load a liquid material (e.g. a hydrophobic conditioning agent), a transfer pipette is used to transfer 2 ml of the liquid material onto the center surface of the Peltier plate. To load a non-liquid material (e.g. a carrier material), 2 grams of non-liquid material is added onto the center surface of the Peltier plate, and the sample is allowed to completely liquefy. If the loaded sample liquid contains visible bubbles, a period of 10 minutes is waited to allow the bubbles to migrate through the sample and burst, or a transfer pipette can be used to extract the bubbles. If bubbles still remain, then the sample is removed from the plate, the plate is cleaned with isopropanol wipe and the solvent is allowed to evaporate away. The sample loading procedure is then attempted again and repeated until a sample is loaded successfully without containing visible bubbles.

The parallel plate is lowered into position in several stages, with the gap distance initially set at 3000 micrometers. After waiting 60 seconds with the plate at that gap distance, the parallel plate is further lowered into position with the gap distance set at 1500 micrometers. After waiting an additional 60 seconds, the parallel plate is further lowered into position with the gap distance set at 750 micrometers. After waiting a final 60 seconds, the parallel plate is further lowered into position with the gap distance set at 550 micrometers.

After the parallel plate is locked, any excess sample material is removed from the perimeter of the parallel plate using rubber policeman. It is important to ensure that the sample is evenly distributed around the edge of the parallel plate and there is no sample on the side or top of plate. If there is sample material on the side or top of the plate, this excess material is gently removed. The Solvent Trap Cover is carefully applied over the parallel plate, and the parallel plate is lowered into its final position by setting the gap distance to 500 micrometers.

The Instrument Procedures and Settings (IPS) used are as follows:
1) Conditioning Step (pre-condition the sample) under the "Environmental Control" label: "Temperature" is 70° C., "Inherit set point" is not selected, "Soak time" is 0.0 s, "Wait for temperature" is selected; under the "Wait for axial force" label: "Wait for axial force" is not selected; under the "Preshear options" label: "Perform preshear" is selected, "Shear rate is $5.0 \text{ s}^{-1}$, "Duration" is 60.0 s, and under the "Advanced" option, the "Motor mode" is Auto; under the "Equilibration" label: "Perform equilibration" is selected, and "Duration" is 120 s.
2) Flow Sweep under the "Environmental Control" label: "Temperature is 70° C., "Inherit set point" is not selected, "Soak time" is 0.0 s, "Wait for temperature" is selected; under the "Test Parameters" label: "Logarithmic sweep" is selected, "Shear rate" is $1.0 \times 10^{-3}$ to $1000.0 \text{ s}^{-1}$, "Points per decade" is 15, "Steady state sensing" is selected, "Max equilibration time" is 45.0 s, "Sample period" is 5.0 s, "% tolerance" is 5.0, "Consecutive within" is 3, "Scaled time average" is not selected; under the "Controlled Rate Advanced" label: "Motor mode" is Auto; under the "Data acquisition" label: "Save point display" is not selected, nor is "Save image" selected; under the "Step termination" label: "Label checking: Enabled" is not selected, nor is "Equilibrium: Enabled" selected.
3) Conditioning End of Test: "Set temperature is selected", "Temperature" is set to 70° C. if running multiple tests, if only running one sample or the last sample, "Temperature" is set to 25° C.; and "Set temperature system idle (only if axial force control is active)" is not selected.

After collecting the data, the data set is opened in the TRIOS software. The limits for the data analysis are set whereby the data points which were collected with an applied rotor torque of less than 1 micro-N·m are discarded, data points which were collected with a measured strain less than 300% are also discarded, and data points which were collected with an applied rotor torque of greater than 20,000 micro-N·m are also discarded.

The remaining data points are analyzed in the following way:
If the relative change (ie variation) in viscosity over the remaining data points is less than 20%, then select the "Analysis" tab from the top tool bar. Select the "Newtonian" option from the "Function" menu. Click the "Start Analysis" button. The viscosity is the "Newtonian Viscosity".
If the relative change in viscosity over the remaining data points equals or exceeds 20%, then select the "Analysis" tab from the top tool bar. Select the "Best Fit Flow (Viscosity vs. Rate)" option from the "Function" menu. Click the "Start Analysis" button. The analysis will show multiple results from different rheology models.

The best model used to determine the viscosity is the model with largest $R^2$ value that incorporates an "Infinite-Rate Viscosity" (e.g. Carreau-Yasuda Model, Carreau Model and Cross Model). The viscosity is the "Infinite-Rate Viscosity" from the best model.

The reported viscosity value of the component measured is the average (mean) viscosity from three independent viscosity measurements (i.e. three replicate sample preparations) and is expressed in units of Pa·s.

Mean Particle Size Test Method

The mean particle size of the hydrophobic conditioning agent in a consumer product composition of the present invention is determined as follows.

A Horiba Laser Scattering Particle Size and Distribution Analyzer, model LA-930 (Horiba Instruments, Inc., Irvine, Calif., USA) with accompanying software (LA-930 Software, Version 3.73) is used to measure the volume-weighted diameter of particles resulting from the dissolution of the test composition (i.e. consumer product composition) in water. A cuvette-type, static quartz fraction cell (10 mL capacity) is used for all measurements. The fraction cell is placed in a Horiba fraction cell holder model LY-203 (available from Horiba Instruments, Inc., Irvine, Calif., USA).

Within the instrument software, the selected graph conditions are: Density Distribution Graph is Standard; Axis Selection is Log X-Lin Y; Cumulative Distribution Graph is On; Size Class is Passing (Undersize); and Axis Type is Bar. Within the instrument software, the selected display conditions include: Form of Distribution is Standard; and Distribution Base is Volume. The Relative Refractive Index (RRI) value to be selected in the software is determined by the identity of the predominant hydrophobic conditioning agent present (on a wt % basis) in the composition being tested. The RRI code selected is 106a/000i if the predominant hydrophobic conditioning agent in the composition is a silicone material e.g., polydimethylsiloxane or Magnasoft Plus (available from Momentive Performance Materials Inc., Waterford, N.Y., USA). The RRI code selected is 112a000i if the predominant hydrophobic conditioning agent in the composition is polyisobutene (such as REWOPAL PIB 1000, available from EVONIK Industries AG, Essen, Germany). For test compositions wherein the predominant hydrophobic conditioning agent is not a silicone material and is not polyisobutene, then the selection of RRI code is determined by first calculating the refractive index ratio for the predominant hydrophobic conditioning agent in the composition versus water, via the equation:

$$\text{Refractive Index Ratio} = \eta_{oil}/\eta_{water}$$

wherein;
$\eta_{water}$=1.3330, and
$\eta_{oil}$=refractive index value (at 20° C. and wavelength of 598 nm) of the predominant (by wt %) hydrophobic conditioning agent in the composition.

If the refractive index value of the predominant hydrophobic conditioning agent is unknown, then a refractometer is used to measure its refractive index at 20° C., using monochromatic light at a wavelength of 598 nm Once the refractive index ratio is determined, the RRI code selected within the Horiba software is the RRI code whose first three numerals match the first three numerals of the refractive index ratio value, and where the RRI code also ends in "/000i".

If there is no RRI code available which exactly matches the first three numerals of the refractive index ratio, then the RRI code selected is the code whose first three numerals represent the next highest value available for selection, which is greater than the first three numerals of the refractive index ratio value, and where the RRI code also ends in "/000i".

Prior to collecting measurements, the initial alignment for the instrument is set for Coarse alignment of the laser beam, and then the alignment is set for Fine alignment with filtered distilled (DI) water loaded in the background reference fraction cell. The filtered DI water background sample is then subtracted by selecting "blank" in the software. Neither the test composition sample, nor the DI water background sample is stirred during the blanking or measurement processes.

Compositions are prepared for testing by being dissolved in filtered distilled (DI) water. Initially, a dispersion with a final concentration of 0.08% (wt/wt) of the test composition in water is prepared and assessed. This initial sample dispersion is prepared by adding 0.08 g of the test composition into 100 g of the filtered DI water at 23° C.±2° C. contained within a flat-bottom glass jar of approximately 200 mL volume. The mixture is then stirred at a rate of approximately 200 rpm until dissolution of the sample is deemed to be complete, as determined when visual inspection reveals that no solid material remains, or when no further dissolution is observable over a time span of 15 minutes. This preparation results in a sample dispersion of water-immiscible particles in filtered DI water, and is the initial sample dispersion to be assessed in the instrument.

A 10 mL aliquot of the sample dispersion is used to rinse the fraction cell of the instrument, and another 10 mL aliquot of the dispersion is loaded into the fraction cell for testing. The initial sample dispersion created is tested in accordance with the instructions and instrument parameters provided above, in order to assess the Laser T % and Lamp T % values reported by the instrument for that sample concentration. These T % values are used to determine if the concentration of the test composition in the initial sample dispersion is suitable for conducting particle size measurements. The goal is to create a sample dispersion whose concentration produces values for both the Laser T % and Lamp T % parameters which fall within the range of 70% to 95%, as this indicates that the dispersion is of a suitable concentration to measure particle diameter. Frequently, the T % values will fall within the suitable range when the total final concentration of the particle-forming material(s) in the dispersion is in range of 0.01% to 0.1% (wt/wt). The T % values reported by the instrument are used to adjust the concentration of the test composition in the dispersion, such that a concentration is identified which is suitable for conducting particle size measurements. This is achieved by creating new test dispersions made at final concentrations either higher or lower than 0.08% accordingly, as needed in order to achieve T % values within the required range. Once a suitable concentration for the dispersion has been determined, new preparations at that concentration are created according to the mixing conditions specified above, for the purpose of conducting the particle diameter measurements in accordance with the instructions and instrument parameters specified.

Each composition being tested is prepared and measured in at least three replicate dispersions at a suitable concentration. Each replicate sample is weighed and dissolved separately, and each replicate dispersion is measured after performing a rinse step with that preparation. Since a prepared dispersion may not be stable, all testing of samples from a dispersion is conducted within the 15 min time period immediately after the dissolution is deemed complete and the stirring has ceased. From each of the three dispersions, two 10 mL aliquots are measured. Each aliquot is measured repeatedly via three analysis runs, such that particle size data is generated three times for each aliquot. This results in six particle size analysis runs for each of the three replicate dispersions. After each particle size measurement analysis run, the instrument software displays a volume-weighted plot of Frequency (%) versus Diameter (µm) as well as the value of the mean volume-weighted particle diameter. The mean volume-weighted particle diameter values measured from all analysis runs of all replicate dispersions, are recorded and averaged, to yield the mean volume-weighted particle size diameter reported as the mean particle size of the hydrophobic conditioning agent of the test composition.

Interfacial Tension Test Method

The interfacial tension (IFT) between a hydrophobic conditioning agent and a liquified carrier material of the non-porous dissolvable solid structure is determined as follows.

Interfacial tension (IFT) measurements are conducted between a hydrophobic conditioning agent and a liquified carrier material using the pendant drop method. If it is impossible to create a drop in the pendant drop instrument (because the interfacial tension is too low), the measurements are then conducted by the spinning drop method.

To conduct IFT measurements, it is necessary to first determine the density of the hydrophobic conditioning agent portion and the density of the liquified carrier material portion of the consumer product composition. A suitable instrument for these density measurements is an Anton Paar DMA 4100 Density Meter (Anton Paar, Graz, Austria). Each test sample of a given portion (hydrophobic conditioning agent and liquified carrier material) of the consumer product composition is heated to 70° C., loaded into a 10 ml syringe and injected into the Density Meter. The injected sample is visually checked to ensure there are no air bubbles in the instrument prior to starting the measurement. The measured density of the sample is recorded from the instrument display panel.

Using the pendant drop method, interfacial tension measurements are made by analyzing the shape of a pendant drop between the hydrophobic conditioning agent and liquified carrier material, suspended at the end of a capillary tube. The pendant drop (hanging from a capillary tube) deforms under its own weight and an image of the drop is captured and analyzed. Comparison of the local curvature associated with the drop shape at different points along the curve provides a measure of the interfacial tension. A suitable instrument for these IFT includes the Krüss Drop Shape Analysis System DSA100 (Krüss, Hamburg, Germany)

To conduct pendant drop IFT measurements, the lower-density portion sample of the consumer product composition is brought to 70° C. inside the drop-shape analysis instrument reservoir. The higher-density portion of the consumer product composition is placed in instrument's capillary tube, and a small drop of the higher-density portion is extruded from the capillary tube into the reservoir. IFT measurements are obtained from images of the drop when its size is about 90% of its weight at detachment (as determined by the continuous addition of more fluid). Approximately three hundred points along the outline of the drop's silhouette are analyzed by the instrument software to determine the local curvature at each point. Pair-wise comparison of data from the points results in approximately 150 measures of the interfacial tension, per drop. From this analysis the instrument reports a single mean value for the interfacial tension for a single drop. The process is repeated for a minimum of five drops. The average IFT value from the five or more replicates is reported, in units of N·m$^{-1}$.

If the denser portion of the consumer product composition fails to form a pendant droplet at the end of the instruments capillary tube, and instead forms a stream of fluid, then the interfacial tension measurements are conducted via the spinning drop method. One instrument suitable for these spinning drop IFT measurements is the Krüss SITE04 Instrument (Krüss, Hamburg, Germany).

To conduct spinning drop IFT measurements, a small drop of the lower-density portion of the consumer product composition is placed inside a barrel (or column) located within the higher-density portion of the consumer product composition (or 'continuous phase'). The barrel is spun causing the drop to elongate along the axis of rotation. The resulting cross-sectional radius (normal to the axis of rotation) is linked to the interfacial tension.

To make these measurements, the higher-density portion (continuous phase) is brought to 70° C. in the barrel, and 3 μL of the lower-density portion is introduced into the barrel. The barrel is rotated at a minimum of five different rotational speeds selected between 1,000-10,000 RPM. The five rotation speeds selected each deform the drop such that $0.9 > R/R_o > 0.75$, where R is the short radius of the drop orthogonal to the rotational axis at the rotational speed, and $R_o$ is the radius of the drop at rest. At each rotational speed, the spinning is held for 10 minutes in order for the drop shape to reach equilibrium, then the radius of the drop is measured and the interfacial tension is calculated. The reported interfacial tension value is the average of all values calculated at the different rotational speeds, and is expressed in units of N·m$^{-1}$.

Dispersion Test Method

The rate of dispersion of the carrier portion of the non-porous dissolvable solid structure of the consumer product composition is determined according to the following test method.

A magnetic stir bar and 200 mL of deionized water (DI water) are placed into a 250 mL capacity glass beaker located on top of a stir plate set at a stir speed of 150 rpm. The temperature of the DI water is maintained between 23° C. and 25° C. A single sample of the consumer product composition (e.g. a single bead) is added into the beaker of stirred DI water, and a timer is started immediately at the same time. The sample (e.g. bead) is then observed visually by eye under well-lit laboratory conditions without the aid of laboratory magnification devices, in order to monitor and assess the appearance and size of the sample (e.g. bead) with regard to its dispersion and disintegration. This visual assessment may require the use of a flash light or other bright light source to ensure accurate observations.

The visual assessment is conducted every 10 seconds over the 60 minute time period after the addition of the sample to the water. If the dispersion of the sample results in the sample becoming visually undetectable as a discrete object(s), then the time point at which this first occurs is noted. If the dispersion of the sample results in a stable visual appearance after which no additional dispersion or disintegration is observed, then the time point at which this stable appearance first occurs is noted. A value of 60 min is assigned if the sample is still visible at the 60 minutes time point and it appeared to still be undergoing dispersion or disintegration immediately prior to the 60 min time point. For each material being tested, the assessment is repeated ten times to result in ten replicate measurements. The time values noted for the ten replicates are averaged, and this average value is reported as the Dispersion Time value determined for that test material.

Molecular Weight Test Method

The molecular weight of a PEG material is determined according to the following test method.

Matrix-Assisted Laser Desorption Ionization Time-Of-Flight (MALDI-TOF) is used in this test method. Mass Spectrometry is a soft ionization technique that can be used for the analysis of molecular weight of biomolecules such as proteins and large organic molecules such as polymers. In MALDI, the analyte is first mixed and co-crystallized with a UV absorbing matrix such as alpha-cyano-4-hydroxycinnamic acid (CHCA), then subjected to pulse laser (YAG or nitrogen laser) radiation. Ions generated are transmitted into a mass analyzer for detection.

To measure the distribution of molecular weights and determine the molecular weight (Mw) to report for a polymer material, between 2 mg and 3 mg of polymer sample are weighed out in a plastic microcentrifuge tube and dissolved in 1 mL of deionised water (DI water). After mixing thoroughly on a vortex mixer, the sample is further diluted 10 times with DI water. Five microliters of the dilute sample solution is mixed with 5 uL of MALDI matrix α-cyano-4-hydroxycinnamic acid solution (i.e., 10 mg/mL CHCA in 80% acetonitrile/water (vol/vol), with 0.1% trifluroacetic acid (vol/vol)), then 1 uL of 50 mM potassium chloride is added and the mixture is thoroughly mixed. One microliter of this mixture is spotted onto a MALDI stainless steel plate and allowed to dry in air at room temperature immediately prior to MALDI analysis. A MALDI-TOF/TOF (such as the model 4800 Plus system from AB-Sciex, Framingham, Mass., U.S.A.) is used in the positive ion linear mode to collect molecular weight measurements. The AB-Sciex MALDI-TOF/TOF 4800 Plus mass spectrometer uses a 200 Hz frequency Nd:YAG laser, operating at a wavelength of 355 nm and with the laser intensity set at 4500 V. Ions generated by the MALDI process are accelerated at 20 kV. MALDI mass spectra are generated in the mass range 5000-12000 Da. Data is collected in an automated fashion using random sampling over the sample spot to collect a total of 1000 shots per spectrum. The molecular weights measured are plotted as a MALDI spectrum histogram displaying the frequency distribution of molecular weight values measured in the sample. The molecular weight value reported for the sample is the molecular weight value corresponding to the top of the peak in the plotted distribution.

EXAMPLES

The following are non-limiting examples of consumer product compositions of the present invention. The consumer product compositions are preferably utilized to treat fabrics by adding the consumer product composition to a clothes washing machine during the wash cycle of a laundry process. In the examples below, the carrier materials are PEG materials available from BASF under the trade name PLUORIOL. In the following examples, all amounts of hydrophobic conditioning agent and carrier material are expressed as weight percent, by weight of the consumer product composition, unless otherwise specified. All viscosities are provided in Pa·s, unless otherwise specified.

|  | 1 | 2 | 3 | 4 | 5 | 6 | 7 | 8 |
|---|---|---|---|---|---|---|---|---|
| Hydrophobic Conditioning Agent ("HCA"): | | | | | | | | |
| MAGNASOFT PLUS [1] | 5 | 5 | 20 | 20 | 20 | 33.3 | 33.3 | 33.3 |
| Carrier Material: | | | | | | | | |
| PEG 8000 | 47.5 | 95 | 80 | 72 | 40 | 33.35 | 66.7 | 60.03 |
| PEG 400 | 47.5 | | | | | 33.35 | | |
| PEG 20000 | | | | 8 | 40 | | | 6.67 |
| Composition Properties: | | | | | | | | |
| Viscosity of HCA @ 25° C. | 3.0 | 3.0 | 3.0 | 3.0 | 3.0 | 3.0 | 3.0 | 3.0 |
| Viscosity of HCA @ 70° C. | 1.3 | 1.3 | 1.3 | 1.3 | 1.3 | 1.3 | 1.3 | 1.3 |
| Viscosity of Carrier Material @ 70° C. | 0.26 | 1.32 | 1.32 | 2.42 | 7.24 | 0.26 | 1.32 | 2.42 |
| Viscosity Ratio @ 70° C. | 5.0 | 0.98 | 0.98 | 0.54 | 0.18 | 5.0 | 0.98 | 0.54 |
| IFT (mN/m) HCA/PEG @ 70° C. | 8.08 | 9.23 | 9.23 | — | — | 8.08 | 9.23 | — |
| Mean Particle Size of HCA (μm) | 36.8 | 2.0 | 11.8 | 11.4 | 7.2 | 95.5 | 25.8 | 18.2 |
| Modified Capillary Number | — | −0.174 | −0.131 | — | — | — | 1.507 | — |

[1] Terminal aminosilicone available from Momentive Performance Materials Inc.

|  | 9 | 10 | 11 | 12 | 13 | 14 | 15 | 16 | 17 |
|---|---|---|---|---|---|---|---|---|---|
| Hydrophobic Conditioning Agent ("HCA"): | | | | | | | | | |
| Polydimethylsiloxane (5 Pa · s) [1] | 5 | 5 | 33.3 | 33.3 | — | — | — | — | — |
| Polydimethylsiloxane (50 mPa · s) [2] | — | — | — | — | 5 | 5 | — | — | — |
| Polydimethylsiloxane (100 Pa · s) [3] | — | — | — | — | — | — | 5 | 5 | 33.3 |
| Carrier Material: | | | | | | | | | |
| PEG 8000 | 95 | 47.5 | 66.7 | 33.35 | 47.5 | 95 | 95 | 47.5 | 66.7 |
| PEG 400 | — | 47.5 | — | 33.35 | 47.5 | — | — | 47.5 | — |
| Composition Properties: | | | | | | | | | |
| Viscosity of HCA @ 25° C. | 4.9 | 4.9 | 4.9 | 4.9 | 0.043 | 0.043 | 96.7 | 96.7 | 96.7 |
| Viscosity of HCA @ 70° C. | 2.12 | 2.12 | 2.12 | 2.12 | 0.021 | 0.021 | 48.3 | 48.3 | 48.3 |
| Viscosity of Carrier Material @ 70° C. | 1.32 | 0.26 | 1.32 | 0.26 | 0.26 | 1.32 | 1.32 | 0.26 | 1.32 |
| Viscosity Ratio @ 70° C. | 1.61 | 8.15 | 1.61 | 8.15 | 0.081 | 0.016 | 36.6 | 185.7 | 36.6 |
| IFT (mN/m) HCA/PEG @ 70° C. | 10.91 | 9.67 | 10.91 | 9.67 | 8.68 | 10.42 | 8.46 | 6.79 | 8.46 |
| Mean Particle Size of HCA (μm) | 5.2 | 37.4 | 26.1 | 38.4 | 10.2 | 12.6 | 14.6 | 15.0 | 48.6 |

[1] Polydimethylsiloxane, trimethylsiloxy terminated, having a viscosity of 5,000 cSt (5 Pa · s) available under the tradename DMS-T35 from Gelest, Inc.
[2] Polydimethylsiloxane, trimethylsiloxy terminated, having a viscosity of 50 cSt (0.05 Pa · s) available under the tradename DMS-T15 from Gelest, Inc.
[3] Available from Dow Corning under the trade name DC200 Fluid 100000 cSt or XIAMETER PMX-200 Silicone Fluid 100000 cSt.

|   | 18 | 19 | 20 |
|---|---|---|---|
| Hydrophobic Conditioning Agent ("HCA"): | | | |
| Y14945[1] | 5 | 5 | 33.3 |
| Carrier Material: | | | |
| PEG 8000 | 95 | 47.5 | 66.7 |
| PEG 400 | — | 47.5 | — |
| Composition Properties: | | | |
| Viscosity of HCA @ 25° C. | 14.5 | 14.5 | 14.5 |
| Viscosity of HCA @ 70° C. | 6.28 | 6.28 | 6.28 |
| Viscosity of Carrier Material @ 70° C. | 1.32 | 0.26 | 1.32 |
| Viscosity Ratio @ 70° C. | 4.75 | 24.2 | 4.75 |
| IFT (mN/m) HCA/PEG @ 70° C. | 9.34 | 7.64 | 9.34 |
| Mean Particle Size of HCA (μm) | 5.9 | 34.6 | 25.9 |

[1]Aminosilicone having a viscosity of about 14,500 cPs (14.5 Pa · s) and an amine content of 0.050 meq/g (Product Code 65850 Y-14945 available from Momentive Performance Materials Inc.)

|   | 21 | 22 |
|---|---|---|
| Hydrophobic Conditioning Agent ("HCA"): | | |
| REWOPAL PIB 1000 (Polyisobutene)[1] | 5 | 5 |
| Carrier Material: | | |
| PEG 8000 | 95 | 47.5 |
| PEG 400 | — | 47.5 |
| Composition Properties: | | |
| Viscosity of HCA @ 25° C. | 23.4 | 23.4 |
| Viscosity of HCA @ 70° C. | 0.86 | 0.86 |
| Viscosity of Carrier Material @ 70° C. | 1.32 | 0.26 |
| Viscosity Ratio @ 70° C. | 0.65 | 3.31 |
| IFT (mN/m) HCA/PEG @ 70° C. | 5.98 | 4.31 |
| Mean Particle Size of HCA (μm) | 3.02 | 9.45 |

[1]Available from Evonik Industries AG

The consumer product compositions in Examples 1-22 above are generally made according to the following process. All materials that are solid at room temperature (23±2° C.) are melted in an 80±5° C. oven and weighed as a heated liquid ("liquified materials"). All materials that are liquid at room temperature are weighed at room temperature. All materials that are liquid at room temperature are added first to a 60 MAX speed mix container (Flacktek, Inc., Landrum, S.C., USA). The targeted weight of carrier materials that are liquid at room temperature are added first, then hydrophobic conditioning agent(s) (e.g. Magnasoft Plus silicone fluid) is added, and then the targeted weight of carrier materials that are liquified materials are added to the same container. The container, which is sealed closed with a plastic lid, is placed in an 80±5° C. oven until the contents reach the oven temperature and become liquefied. The container is then removed from the oven, placed in a 60 max speed mixer holder, and speed mixed for 30 seconds at 3500 rpm in a Flacktek DAC150.FVZ-K speed mixer (Flacktek, Inc., Landrum, S.C., USA).

Figure 4:
FIG. 4 is a photograph of a consumer product of the present invention in the form of a plurality of beads.

The resulting melt composition is then transferred (by pouring and scraping sides of container with a metal spatula) onto an appropriate surface, for example aluminum foil or a preheated mold (at 80° C.) with indentations to form non-porous dissolvable solid structures in the form of a plurality of beads having hemispherical shapes. A six or twelve inch flexible joint knife is used to evenly spread the composition into the mold indentations. The melt composition is then allowed to cool to room temperature to solidify, at which time the solid composition is removed from the aluminum foil or removed from the mold. The resulting consumer product composition in the form of a plurality of beads having hemispherical shapes is illustrated in FIG. 4.

Comparative Example 1

A consumer product composition similar to Example 7 above (33.3% MAGNASOFT PLUS and 66.7% PEG 8000) above is prepared except that instead of using 100% aminosilicone fluid as a conditioning agent, the aminosilicone fluid is first emulsified according to the following emulsion preparation.

Weigh out 100 grams aminosilicone (MAGNASOFT PLUS), 6.67 grams of a first emulsifier (Tergitol TMN-6) and 4 grams of a second emulsifier (Lutensol XL70), and mix together. Apply shear using a homogenizer (available from Silverson) set to 4500 rpm. Scrape cup walls to provide complete mixing. Add 20 grams of water slowly and mix until a homogeneous mixture is obtained. Add 68.65 grams of additional water slowly while continue to mix for at least 15 minutes increasing rpm as needed (viscosity increase will happen during phase inversion requiring to increase mixing speed). Check pH and adjust as required using acetic acid to reach a pH value of 5-6. The resulting aminosilicone emulsion is then incorporated into the consumer product composition according to the following formulation (made according to the process for making Examples 1-22 above):

|   | Comparative Example 1 |
|---|---|
| 50% MAGNASOFT PLUS Emulsion | 40.0 |
| Carrier Material: | |
| PEG 8000 | 60.0 |

The aminosilicone conditioning agent of the resulting consumer product composition has a mean particle size of 1 micron, which is much lower than the mean particle size of the conditioning agent of Example 7. This is believed to be due to the pre-emulsification of the conditioning agent before adding to the consumer product composition, which is typical of conventional consumer product compositions containing aminosilicones.

Fabric Conditioning Performance

The following illustrates the fabric conditioning performance (e.g. fabric softness) of consumer products of the present invention in comparison with Tide® Free and Gentle™ Liquid Laundry Detergent ("Tide"), Comparative Example 1 above, and Ultra Downy® Clean Breeze with Silk Touch™ Liquid Fabric Softener ("Downy") (added through the rinse). The product compositions were tested via a coefficient of friction test method as follows, to indicate the level of fabric conditioning provided by the respective product compositions.

Coefficient Of Friction ("COF") measurements are made on fabrics treated with the softening composition in the following way. The following fabrics are added to a Whirlpool Duet HT front loading HE washer (constituting a "load"): nine 100% cotton t-shirts, nine 100% cotton towels, and nine 50% cotton/50% polyester pillow cases, and twelve 100% cotton China 2 terry towels ("terry towels"), then the load is adjusted to approximately 8.5 lbs. by removing terry towels as needed. For test compositions, Tide detergent in the amount of 50.0 grams is added to the dispenser of the washer and an appropriate amount of the consumer product composition of the present invention (or the comparative example) is added directly to the drum of the washer in an amount to provide 2 grams of hydrophobic conditioning agent. For the Tide detergent control, only 50.0 grams of Tide detergent is added. For the Downy softener control, 50.0 grams of Tide detergent are added and then, during the rinse cycle, 35.7 grams of Downy softener are dispensed into the rinse. The washer is run with the following machine settings: setting: "Normal Wash"; wash temperature: 100° F.; rinse temperature: 70° F. with both wash/rinse water containing six grains-per-gallon hardness. Upon completion of the wash and rinse cycles, the entire load is tumble dried for 50 minutes. The process is repeated for three complete wash and dry cycles.

Once completed, two 6.5 cm×13 cm swatches are cut from each of the terry towels and two swatches from the same terry towel are placed in a Thwing Albert FP-2250 friction tester (Thwing Albert Instrument Company, 14 W. Collings Avenue, West Berlin, N.J. 08091). A 200 gram weight is placed on the top swatches and the dynamic friction is tested at 200 mm/min for 20 seconds. The reported value of COF for a particular test sample is the average dynamic friction taken on eight terry towels from the load.

A consumer product composition of the present invention (made according the process described above for Examples 1-22) which has the formula:

|  | Example 23 |
|---|---|
| Hydrophobic Conditioning Agent ("HCA"): | |
| MAGNASOFT PLUS | 33.3 |
| Carrier Material: | |
| PEG 8000 | 61.7 |
| PEG 400 | 5.0 |

Figure 5:
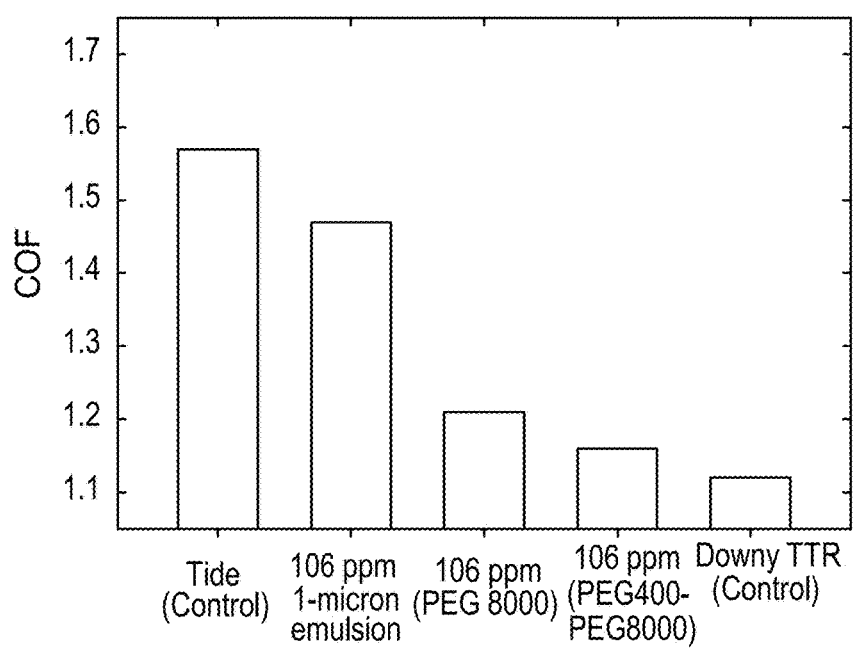
FIG. 5 is a plot of coefficient of friction provided by consumer product compositions of the present invention in comparison to control products.

(referred to herein as Example 23) and a consumer product composition of Example 7 are tested according to the COF method above, along with the following compositions as controls: Tide, Downy and Comparative Example 1. The results of the test are shown in FIG. 5. The results demonstrate that the Comparative Example 1 provides very little fabric conditioning performance relative to the Tide detergent control, while the consumer product compositions of the present invention provide fabric conditioning performance nearly as good as Downy liquid softener added through the rinse. This level of fabric conditioning performance via a consumer product added through the wash cycle is surprising and believed to result from the relatively large mean particle size of conditioning agent provide within the consumer product composition of the present invention and upon dissolution in the subsequent aqueous treatment liquor in the wash cycle.

The following test illustrates the fabric conditioning performance (e.g. fabric softness) of consumer product compositions of the present invention with respect to varying levels of hydrophobic conditioning agent in the consumer product composition, compared to Tide detergent and Downy softener. The relative coefficient of friction (COF) data is determined by the COF method above, except that (i) the consumer product composition is added in an amount to provide 3 grams of hydrophobic conditioning agent (instead of 2 grams), and (ii) all COF values for compositions of the present invention (test compositions) are referenced to a negative control (only 50 grams of Tide detergent without any fabric conditioning product added in the wash) and to a positive control (50 grams of Tide detergent added in the wash and 35.7 grams Downy liquid softener added in the rinse), wherein the reported "Relative COF" ("COFrel") is expressed as:

$$COFrel = 0.5 \times \left[ \frac{(COF \text{ Test Composition} - COF \text{ Downy})}{(COF \text{ Tide} - COF \text{ Downy})} \right]$$

The consumer product compositions tested include the following: 10% MAGNASOFT PLUS and 90% PEG 8000; 12.5% MAGNASOFT PLUS and 87.5% PEG 8000; 15% MAGNASOFT PLUS and 85% PEG 8000; and 17.5% MAGNASOFT PLUS and 82.5% PEG 8000. Each consumer product composition tested is made according to the process described above for Examples 1-22.

Figure 6:
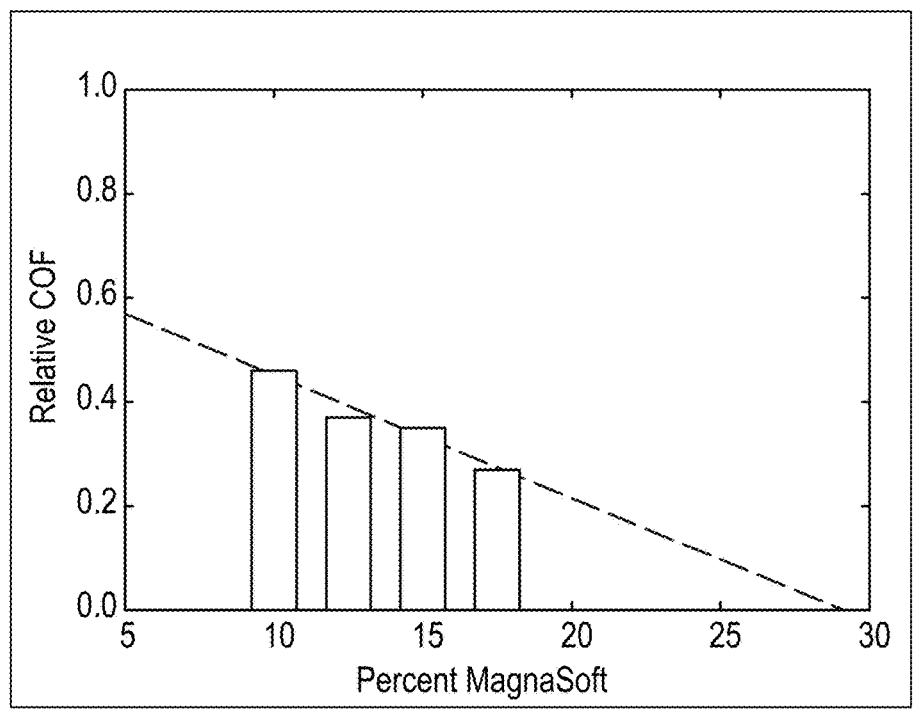
FIG. 6 is a plot of relative coefficient of friction provided by consumer product compositions of the present invention in comparison to control products.

The results of the test are shown in FIG. 6. The results demonstrate that increasing level of hydrophobic conditioning agent in the consumer product composition leads to increased level of fabric conditioning performance, when using the same total amount (e.g. 3 grams) of hydrophobic conditioning agent in the test. Since increasing levels of hydrophobic conditioning agent in the consumer product composition tends to provide larger mean particle size (see, e.g., FIG. 2), these data illustrate that fabric conditioning performance increases (i.e. lower COF) as mean particle size of the hydrophobic conditioning agent increases, when adding equal amounts of hydrophobic conditioning agent in a laundry process.

Consumer-noticeable fabric conditioning performance is typically represented by Relative COF values of about 0.5 or less. As such, preferred levels of hydrophobic conditioning agent in the consumer product composition of the present invention are at least 5%, by weight of the consumer product composition, as illustrated by the data of FIG. 6.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A consumer product composition comprising
a non-porous dissolvable solid structure comprising from about 50% to about 95%, by weight of said consumer product composition, of a carrier material, wherein said carrier material is a polyethylene glycol material having a molecular weight of from about 200 to about 50,000, and from about 12% to about 50%, by weight of said consumer product composition, of a silicone hydrophobic conditioning agent disposed within said polyethylene glycol carrier material, wherein the mean particle size of said silicone hydrophobic conditioning agent disposed within said polyethylene glycol carrier material is from about 2 μm to about 2000 μm;

wherein said consumer product composition comprises less than about 3%, by weight of said consumer product composition, of detersive surfactant and/or cleansing surfactant; and wherein said consumer product composition is in the form of a plurality of beads, having an average maximum cross-sectional dimension of from about 0.05 to about 50mm.

2. The consumer product composition of claim 1, wherein said polyethylene glycol material has a molecular weight of from about 500 to about 20,000.

3. The consumer product composition of claim 1, wherein said polyethylene glycol material has a molecular weight of from about 1,000 to about 15,000.

4. The consumer product composition of claim 1, wherein said consumer product composition comprises from about 12% to about 40%, by weight of said consumer product composition, of said silicone hydrophobic conditioning agent.

5. The consumer product composition of claim 1, wherein said consumer product composition comprises from about 15% to about 40%, by weight of said consumer product composition, of said silicone hydrophobic conditioning agent.

6. The consumer product composition of claim 1, wherein said consumer product composition comprises from about 60% to about 95%, by weight of the consumer product composition, of said polyethylene glycol carrier material.

7. The consumer product composition of claim 1, wherein said silicone hydrophobic conditioning agent has a viscosity at 70° C. of from about 0.1 to about 2000 Pa·s.

8. The consumer product composition of claim 1, wherein said silicone hydrophobic conditioning agent is a liquid at 25° C.

9. The consumer product composition of claim 1, wherein said silicone hydrophobic conditioning agent has a viscosity at 25° C. of from about 0.1 to about 2000 Pa·s.

10. The consumer product composition of claim 1, wherein said polyethylene glycol carrier material has a viscosity at 70° C. of from about 0.005 to about 350 Pa·s.

11. The consumer product composition of claim 1, wherein said polyethylene glycol carrier material has a melting point of from about 25° C. to about 120° C.

12. The consumer product composition of claim 1, wherein said polyethylene glycol carrier material is a solid at 25° C.

13. The consumer product composition of claim 1, wherein a ratio of the viscosity of said silicone hydrophobic conditioning agent at 70° C. to the viscosity of said polyethylene glycol carrier material at 70° C. is from about 1000:1 to about 1:1000.

14. The consumer product composition of claim 1, wherein said polyethylene glycol carrier material disperses completely in 25° C. water within a Dispersion Time of less than 60 minutes.

15. The consumer product composition of claim 1, wherein said polyethylene glycol carrier material disperses completely in 25° C. water within a Dispersion Time of less than about 10 minutes.

16. The consumer product composition of claim 1, wherein the mean particle size of said silicone hydrophobic conditioning agent disposed within said polyethylene glycol carrier material is from about 2 μm to about 500 μm.

17. The consumer product composition of claim 1, wherein the mean particle size of said silicone hydrophobic conditioning agent disposed within said polyethylene glycol carrier material is from about 2 μm to about 120 μm.

18. The consumer product composition of claim 1, wherein said silicone hydrophobic conditioning agent comprises a terminal aminosilicone or a polydimethylsiloxane.

19. The consumer product composition of claim 1, wherein said consumer product composition is in the form of a plurality of beads, having an average maximum cross-sectional dimension of from about 0.3 to about 10 mm.

20. The consumer product composition of claim 1, wherein said consumer product composition is in the form of a plurality of beads, having an average maximum cross-sectional dimension of from about 0.5 to about 5 mm.

21. The consumer product composition of claim 1, wherein said consumer product composition is in the form of a plurality of beads having an average aspect ratio of from about 1:1 to about 1000:1.

22. The consumer product composition of claim 1, wherein said consumer product composition comprises a ratio of the level of polyethylene glycol carrier material to the level of silicone hydrophobic conditioning agent of from about 1:1 to about 20:1.

23. The consumer product composition of claim 1, wherein said consumer product composition comprises less than about 5%, by weight of said consumer product composition, of water.

24. The consumer product composition of claim 1, wherein said consumer product composition further comprises a filler material selected from the group consisting of inorganic salts, carbohydrates, clays, metal oxides, zeolites, silicas, and urea.

25. A method of treating a surface comprising the steps of:
providing a consumer product composition according to claim 1;
providing an aqueous solution;
dissolving said consumer product composition in said aqueous solution to form an aqueous treatment liquor; and
contacting said surface with said aqueous treatment liquor.

* * * * *